United States Patent [19]

Sato et al.

[11] Patent Number: 5,206,129
[45] Date of Patent: Apr. 27, 1993

[54] DYE FORMING COUPLERS, AND A METHOD OF COLOR IMAGE FORMATION AND SILVER HALIDE COLOR PHOTOGRAPHIC PHOTOSENSITIVE MATERIALS IN WHICH THEY ARE USED

[75] Inventors: Kozo Sato; Kiyoshi Takeuchi; Yoshio Ishii, all of Minami Ashigara, Japan

[73] Assignee: Fuji Photo Film Co., Ltd., Minami Ashigara, Japan

[21] Appl. No.: 789,023

[22] Filed: Nov. 7, 1991

[30] Foreign Application Priority Data

Nov. 22, 1990 [JP] Japan .................................. 2-315906

[51] Int. Cl.⁵ ............................................. G03C 7/38
[52] U.S. Cl. ..................................... 430/558; 430/384; 430/385; 430/386; 430/387
[58] Field of Search ............... 430/558, 384, 385, 386, 430/387, 558 A

[56] References Cited

U.S. PATENT DOCUMENTS 5,024,930  6/1991  Kita et al. ............................ 430/558

FOREIGN PATENT DOCUMENTS 0144132  9/1980  Fed. Rep. of Germany ...... 430/558
2-129629  5/1990  Japan .................................. 430/385

*Primary Examiner*—Lee C. Wright
*Attorney, Agent, or Firm*—Burns, Doane, Swecker & Mathis

[57] ABSTRACT

Disclosed is a dye forming coupler represented by formula (I):

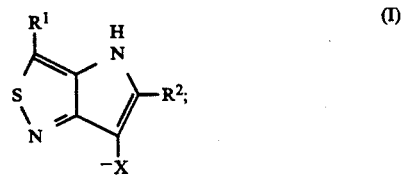

wherein $R^1$ and $R^2$, which may be the same or different, each represents a substituent group, and X is a hydrogen atom or a group which can be eliminated by a coupling reaction with the oxidized species of a primary aromatic amine derivative.

13 Claims, 1 Drawing Sheet

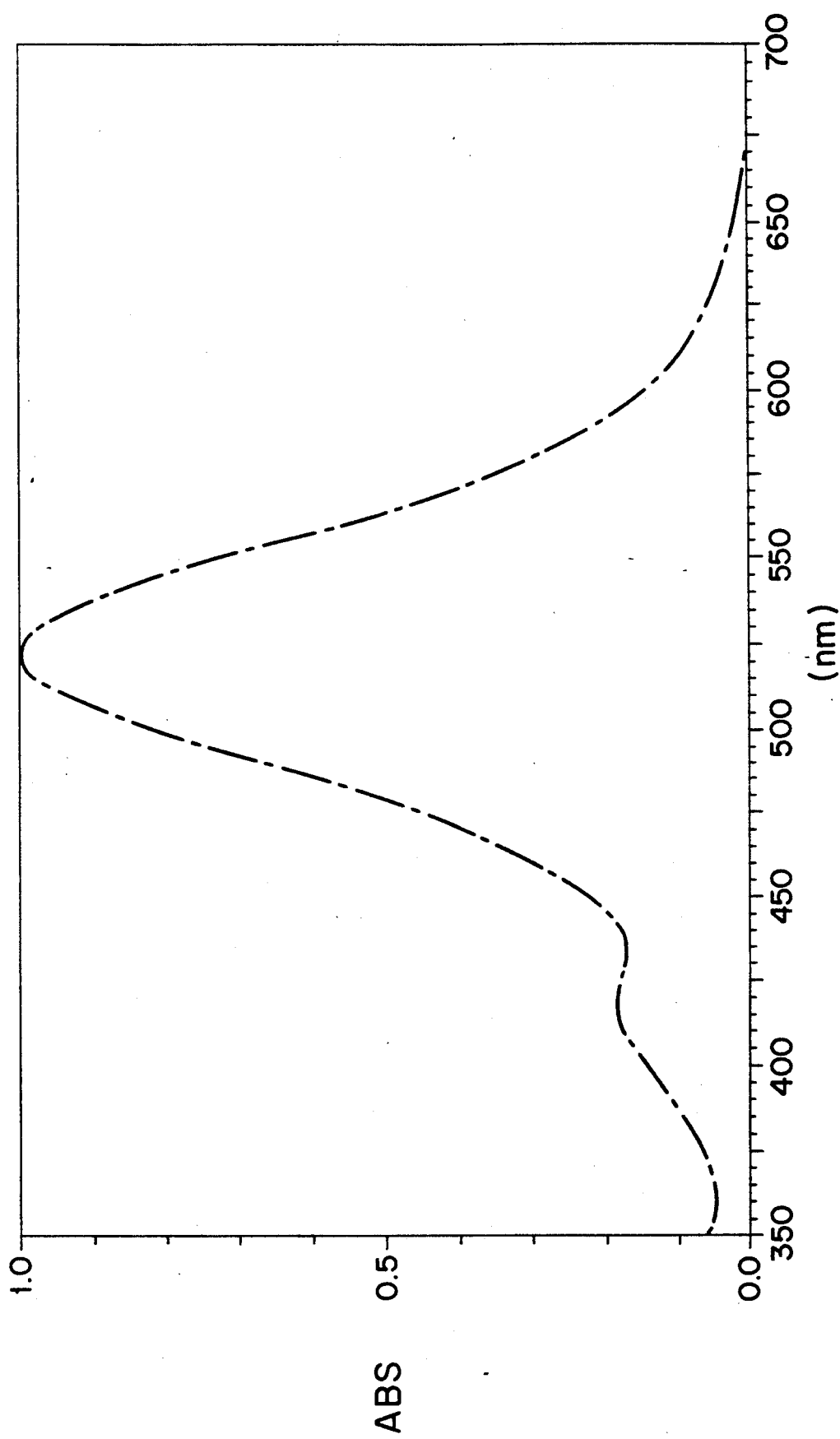

DYE FORMING COUPLERS, AND A METHOD OF COLOR IMAGE FORMATION AND SILVER HALIDE COLOR PHOTOGRAPHIC PHOTOSENSITIVE MATERIALS IN WHICH THEY ARE USED

FIELD OF THE INVENTION

This invention relates to novel dye forming couplers which can be used, for example, in silver halide color photographic photosensitive materials, a method of color image formation in which the couplers are used, and silver halide photographic photosensitive materials which contain the said couplers.

BACKGROUND OF THE INVENTION

The system in which color images are formed using a subtractive color method where reactions occur between color developing agents and dye forming couplers which form the colors yellow, magenta and cyan, is widely used in silver halide color photographic photosensitive materials.

In recent years, there has been a large amount of research associated with improving dye forming couplers, particularly improving color reproduction and image fastness in silver halide color photographic photosensitive materials. Unfortunately, color developing agents are still limited as an adequate improvement has yet to be realized.

Pyrazolone-based or pyrazoloazole-based couplers have been used conventionally as magenta couplers, but the dyes formed from these couplers sometimes have a poor cut-off on the short wavelength side. Furthermore, synthesis of these couplers involves a complicated, multi-stage routine. They cannot be prepared using a short synthetic technique.

Phenol-based couplers and naphthol-based couplers have been used conventionally as cyan couplers, but dyes produced from these couplers have unwanted absorptions in the blue and green region. They present a major obstacle to the improvement of color reproduction.

Recently, research has been actively pursued into cyan dye forming couplers with novel skeletal structures including nitrogen containing heterocyclic rings, and various nitrogen containing heterocyclic compounds have been suggested. For example, diphenylimidazole-based couplers have been disclosed in JP-A-63-226653, and pyrazoloazole-based couplers have been disclosed, for example, in JP-A-63-199352, JP-A-63-250649, JP-A-63-250650, JP-A-64-554, JP-A-64-555, JP-A-1-105250 and JP-A-1-105251. (The term "JP-A" used herein signifies an "unexamined published Japanese patent application".) These couplers all provide improved color reproduction, and they are characterized by excellent absorption characteristics of the dyes which are formed.

However, the dyes which are produced by the above-mentioned couplers sometimes have an absorption wavelength which is biased to the short wavelength side. In addition, they have poor light and heat fastness. Even another serious problem is that the couplers exhibit a low coupling activity in practice.

Accordingly, these problems need to be effectively addressed, not only for photographic dye forming couplers, but for dye forming couplers as well.

SUMMARY OF THE INVENTION

The first object of the present invention is to provide novel couplers which provide colored dyes having excellent absorption characteristics.

Another object of the invention is to provide novel couplers which provide colored dyes having improved fastness.

Even another object of the invention is to provide silver halide color photographic photosensitive materials, and a method of forming color images, wherein the aforementioned difficulties encountered with the conventional couplers are overcome, and in which excellent color reproduction can be obtained, and in which the resulting color image exhibits improved fastness.

The above-described objects of the invention have been obtained by using dye forming couplers represented by formula (I) below, a method of forming color images using those dye forming couplers, and silver halide color photographic photosensitive materials which contain at least one of the color forming couplers.

wherein $R^1$ and $R^2$, which may be the same or different, each represents a substituent group and X represents a hydrogen atom or a group which can be eliminated by a coupling reaction with an oxidized species of a primary aromatic amine derivative.

BRIEF DESCRIPTION OF THE DRAWING

FIGURE 1 shows the absorption spectrum in ethyl acetate solution of the magenta dye formed from the oxidized species of 2-methyl-4-(N-ethyl-N-methanesulfonylethylamino)aniline and coupler (33).

DETAILED DESCRIPTION OF THE INVENTION

The dye forming couplers of the present invention are described in detail below.

In formula (I), $R^1$ and $R^2$, which may be the same or different, each represents a substituent group such as a halogen atom; an aliphatic group preferably having from 1 to 36 carbon atoms; an aromatic group preferably having from 6 to 36 carbon atoms (e.g., phenyl, naphthyl), a heterocyclic group (e.g., 3-pyridyl 2-furyl), an alkoxy group (e.g., methoxy, 2-methoxyethoxy), an aryloxy group (e.g., 2,4-di-tertamylphenoxy, 2-chlorophenoxy 4-cyanophenoxy), an alkenyloxy group (e.g., 2-propenyloxy), an amino group (e.g., butylamino, dimethylamino, anilino, N-methylanilino), an aliphatic or aromatic acyl group (e.g., acetyl, benzoyl), an aliphatic or aromatic oxycarbonyl group (e.g., butoxycarbonyl, phenoxycarbonyl), an aliphatic or aromatic acyloxy group (e.g., acetoxy, benzoyloxy), a aliphatic or aromatic oxysulfonyl group (e.g., butoxysulfonyl, phenoxysulfonyl), an aliphatic or aromatic acylamino group (e.g., acetylamino), a carbamoyl group (e.g., ethylcarbamoyl, dimethylcarbamoyl), an aliphatic or aromatic sulfonamido group (e.g., methanesulfonamido), a sulfamoyl group (e.g., butylsulfamoyl), a sulfamido group (e.g., dipropylsulfamoylamino), an imido group (e.g., succinimido, hydantoinyl), a ureido group (e.g., phenylureido, dimethylureido), an aliphatic or aromatic sulfonyl group (e.g., methanesulfonyl, benzenesulfonyl), an azo group; an aliphatic or aromatic sulfonyloxy group; a phosphoyl group; an aliphatic or aromatic thio group (e.g., ethylthio, phenylthio), an aliphatic or aromatic sulfinyl group (e.g., methanesulfinyl, benzenesulfinyl, naphthalenesulfinyl), a hydroxyl group; a cyano group; a carboxyl group; a nitro group and a sulfo group.

Herein, the term "aliphatic group" signifies a straight chain, branched or cyclic aliphatic hydrocarbyl group, including saturated and unsaturated groups such as alkyl, alkenyl and alkynyl groups, and groups which have been further substituted. Typical examples of such groups include methyl, ethyl, butyl, dodecyl, octadecyl, icosenyl, iso-propyl, tertbutyl, tert-octyl, tert-dodecyl, cyclohexyl, cyclopentyl, allyl, vinyl, 2-hexadecenyl and propargyl groups.

Herein the term "aromatic group" signifies an aryl group which may have a substituent.

$R^1$ and $R^2$ each is preferably a substituent group which substantially cannot be eliminated when reacted with a reaction with the oxidized apecies of a primary aromatic amine derivative. At least one of $R^1$ and $R^2$ in preferred cyan couplers and preferred magenta couplers is an electron withdrawing group having a Hammet substitution constant $\sigma_p$ of at least 0.10 and $R_1$ and $R_2$ each in more preferred cyan couplers is an electron withdrawing group having a Hammett substitution constant $\sigma_p$ of at least 0.10.

The value disclosed in a report by Hansch, C. Leo et al. (for example, J. Med. Chem. 16, 1207 (1973), ibid, 20, 304 (1977)) is preferably used for the value of the Hammett substitution constant $\sigma_p$ referred to herein.

Examples of electron withdrawing groups having a Hammett substitution constant $\sigma_p$ of at least 0.10 include a cyano group, a carbamoyl group (e.g., N-phenylcarbamoyl, N-(2-chloro-5-tetradecyloxycarbonylphenyl)carbamoyl, N,N-diethylcarbamoyl, N-(2,4-dichlorophenyl)carbamoyl, N-(2-chloro-5-hexadecanesulfonamidophenyl)carbamoyl), an alkoxycarbonyl group (e.g., ethoxycarbonyl, butoxycarbonyl, dodecyloxycarbonyl 2-ethylhexyloxycarbonyl), an aryloxycarbonyl group (e.g., phenoxycarbonyl, 1-naphthyloxycarbonyl), an aliphatic or aromatic acyl group (e.g., benzoyl, acetyl, 4-chlorobenzoyl, 2,4-dichlorobenzoyl), an aliphatic or aromatic sulfonyl group (e.g., methanesulfonyl, dodecanesulfonyl, benzenesulfonyl, 2-butoxy-5-tert-octylbenzenesulfonyl), a sulfamoyl group (e.g., N-butylsulfamoyl, N-phenylsulfamoyl, N,N-diethylsulfamoyl), a nitro group; an alkyl group substituted with polyhalogen atoms (e.g., trifluoromethyl, heptafluoropropyl), a sulfinyl group (e.g., methanesulfinyl, benzenesulfinyl, naphthalenesulfinyl), a carboxyl group; an azo group, an alkylsulfonyloxy group, a phosphoryl group, a heterocyclic residual group (e.g., 1-tetrazolyl) and an aryl group which is substituted with a cyano group, an aliphatic or aromatic sulfonyl group, a nitro gorup, or polyhalogen atoms.

In the present invention, electron withdrawing groups having a $\sigma_p$ value of at least 0.35 are preferred for $R^2$ in a cyan coupler, and electron withdrawing groups having value of at least 0.60 are most desirable.

Electron withdrawing groups having a $\sigma_p$ of at least 0.35 include, from the aforementioned groups which have a $\sigma_p$ value of at least 0.10, a cyano group, a carboxyl group, an azo group, a nitro group, an aliphatic or aromatic acyl group, a carbamoyl group, an alkoxycarbonyl group, an alkylsulfonyloxy group, a phosphoryl group, a heterocyclic residual group (e.g., 1-tetrazolyl), a sulfamoyl group, an aliphatic or aromatic sulfonyl group, an alkyl group substituted with polyhalogen atoms and an aryl group which is substituted with a cyano group, a sulfonyl group, a nitro group or polyhalogen atoms.

Electron withdrawing groups having a $\sigma_p$ value of at least 0.60 include a cyano group, a nitro group and an aliphatic or aromatic sulfonyl group.

X in formula (I) represents a hydrogen atom or a group which can be eliminated by a coupling reaction with the oxidized species of a primary aromatic amine derivative (hereinafter a leaving group).

Actual examples of leaving groups include a halogen atoms (e.g., fluorine, chlorine, bromine), an alkoxy group (e.g., ethoxy, dodecyloxy, methoxyethylcarbamoylmethoxy, carboxypropyloxy, methanesulfonylethoxy), an aryloxy group (e.g., 4-chlorophenoxy, 4-methoxyphenoxy, 4-carboxyphenoxy), an aliphatic or aromatic acyloxy group (e.g., acetoxy, tetradecanoyloxy, benzoyloxy), an aliphatic or aromatic sulfonyloxy group (e.g., methanesulfonyloxy, toluenesulfonyloxy), an acylamino group (e.g., dichloroacetylamino, heptafluorobutyrylamino), an aliphatic or aromatic sulfonamido group (e.g., methanesulfonamido, p-toluenesulfonamido), an alkoxycarbonyloxy group (e.g., ethoxycarbonyloxy, benzyloxycarbonyloxy), an aryloxycarbonyloxy group (e.g., phenoxycarbonyloxy), an aliphatic, aromatic or heterocyclic thio group (e.g., ethylthio, phenylthio, tetrazolylthio), a carbamoylamino group (e.g., N-methylcarbamoylamino, N-phenylcarbamoylamino), a five- or six-membered nitrogen-containing heterocyclic group (e.g., imidazolyl, pyrazolyl, triazolyl, 1,2-dihydro-2-oxo-1-pyridyl), an imido group (e.g., succinimido, hydantoinyl), an aromatic azo group (e.g., phenylazo), and a carboxyl group. These groups may be substituted with the groups permitted for the substituent groups $R^1$ and $R^2$. Furthermore, there are bis-type couplers in which four-equivalent couplers are condensed with aldehydes or ketones as leaving groups which are bonded via a carbon atom. The leaving groups of this present invention may contain photographically useful groups such as development inhibitors or development accelerators.

The couplers represented by formula (I) can be used as so-called internal-type couplers which are contained in a silver halide color photographic photosensitive materials, or as so-called external-type couplers which are included in a color developer. At least one of the groups represented by $R^1$, $R^2$ and X in formula (I) is preferably one having a total of from 10 to 50 carbon atoms when the coupler is being used as an internal-type coupler.

Couplers of the present invention are effective as cyan couplers and magenta couplers, and especially effective as cyan couplers.

Actual examples of couplers according to the present invention are indicated below, but the invention is not to be limited by these examples.

(1) 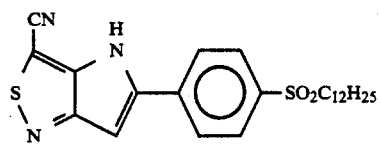
(2) 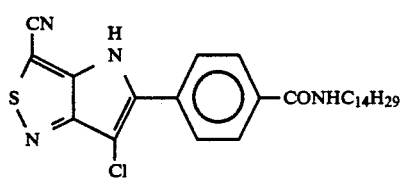
(3) 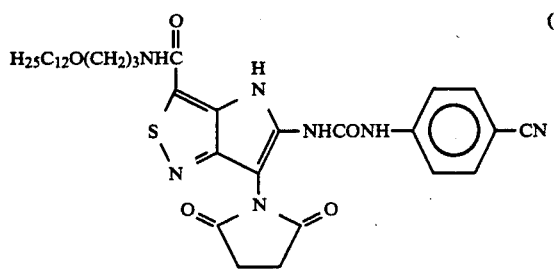
(4) 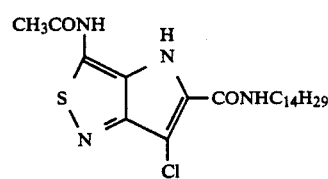
(5) 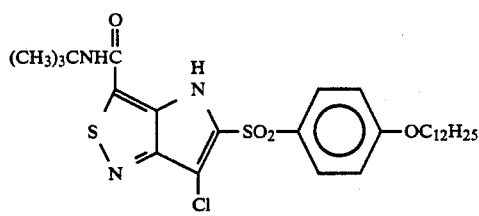
(6) 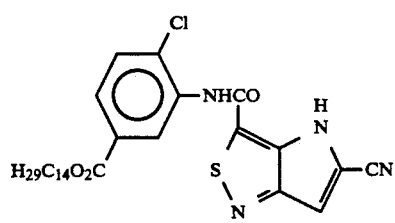
(7) 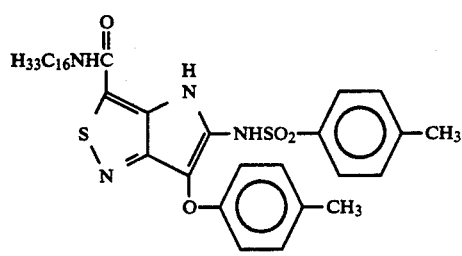
-continued
(8) 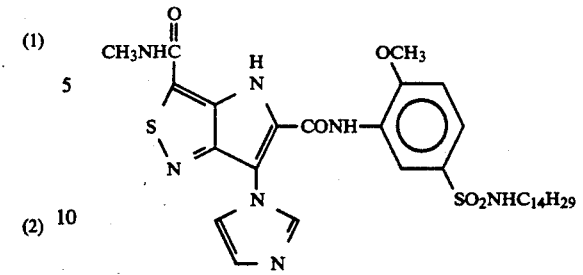
(9) 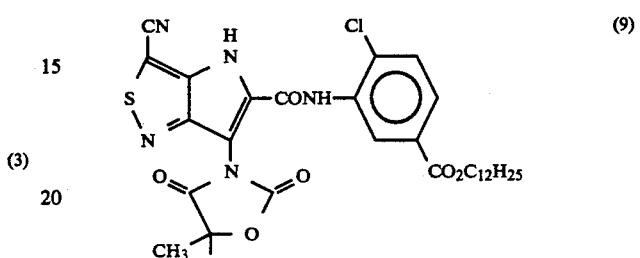
(10) 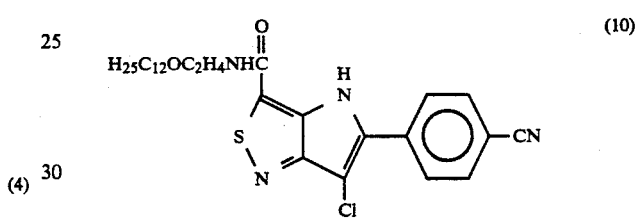
(11) 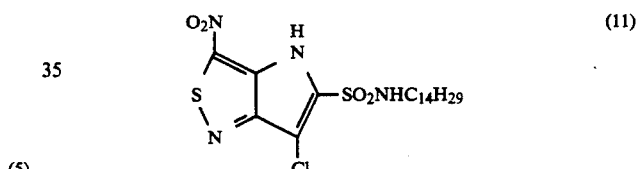
(12) 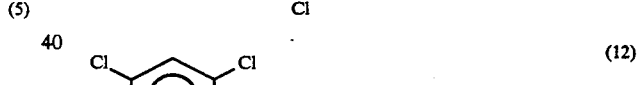
(13) 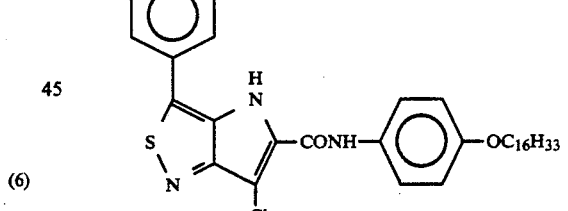
(14) 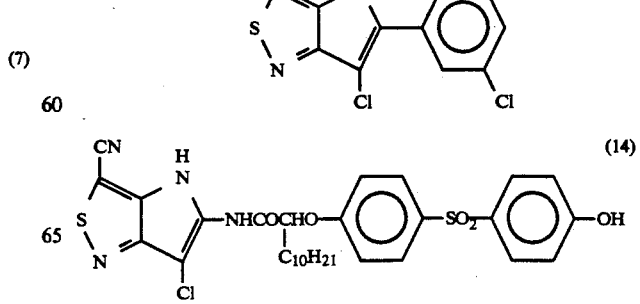

-continued
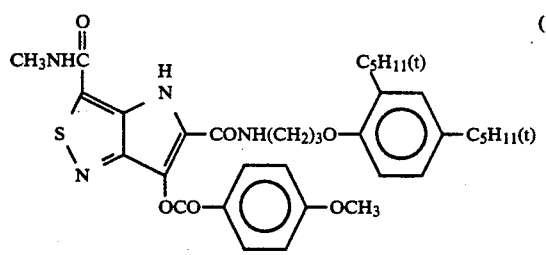 (15)
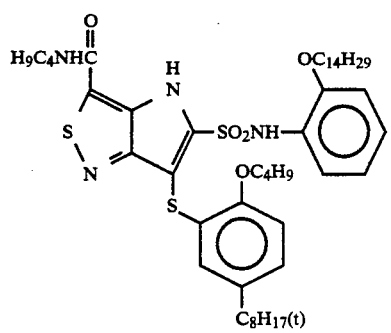 (16)
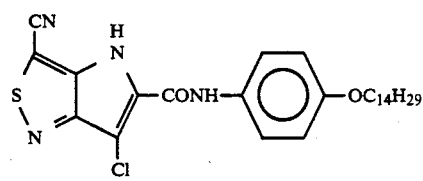 (17)
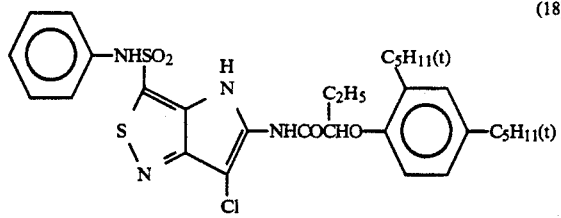 (18)
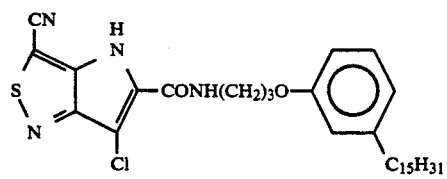 (19)
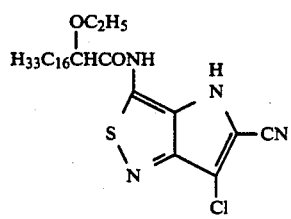 (20)
-continued
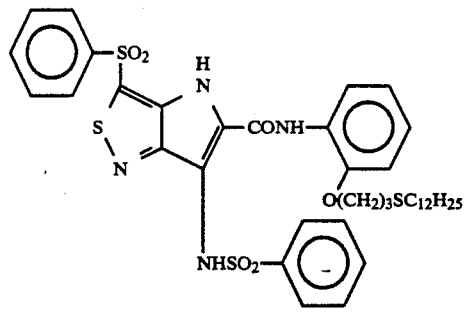 (21)
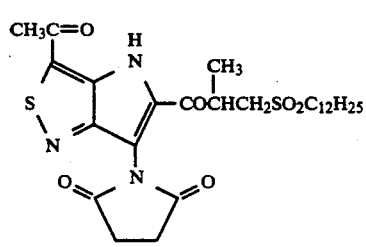 (22)
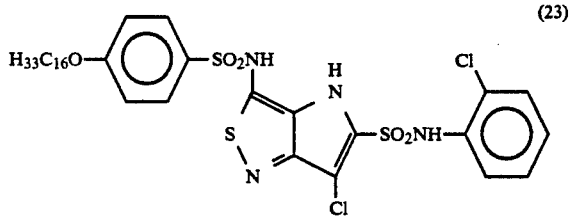 (23)
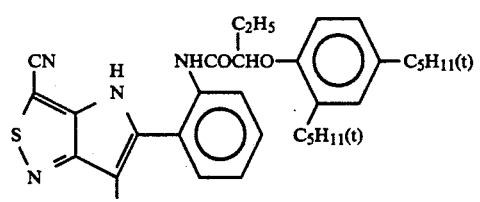 (24)
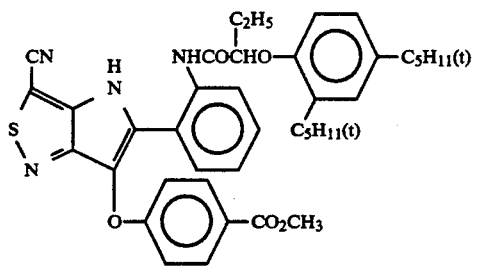 (25)
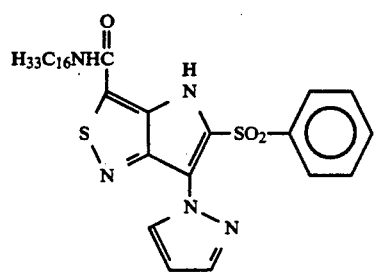 (26)

-continued

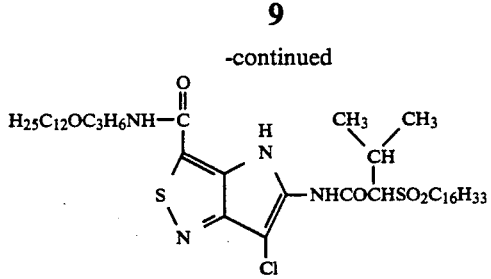
(27)

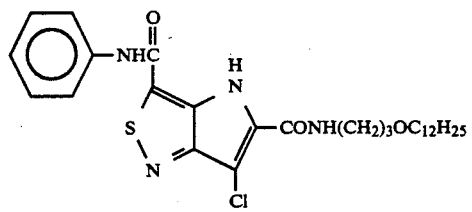
(28)

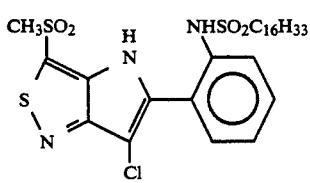
(29)

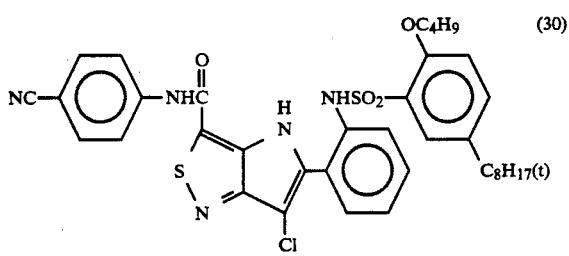
(30)

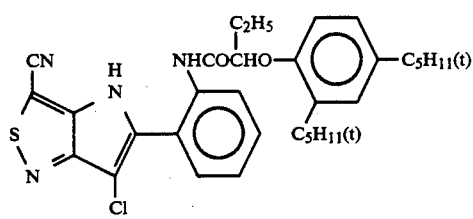
(31)

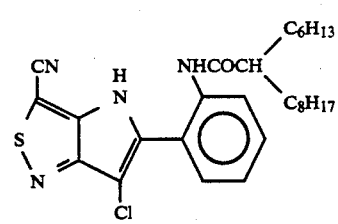
(32)

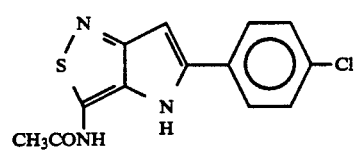
(33)

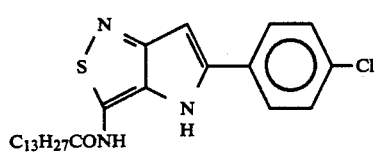
(34)

-continued

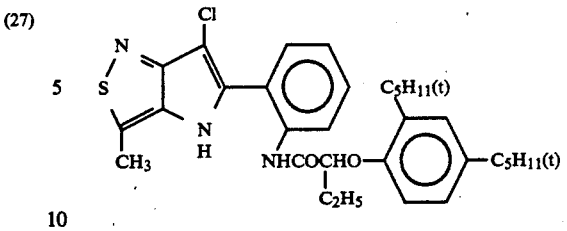
(35)

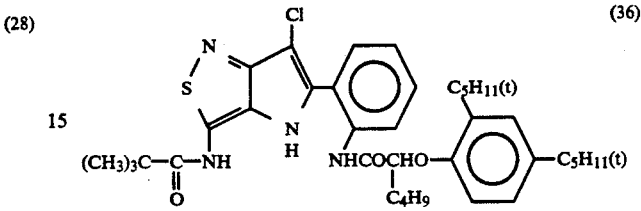
(36)

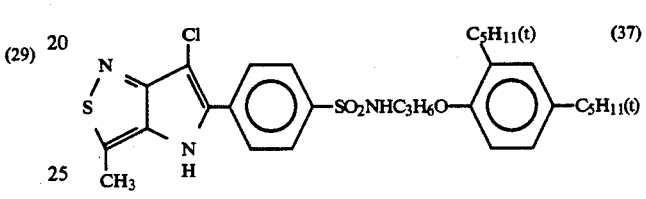
(37)

Examples of the preparation of typical couplers according to the present invention are described below.

SYNTHESIS EXAMPLE 1: (SYNTHESIS OF COUPLER (1))

(1-1) Preparation of 5-Cyano-3-(4-dodecylsulfonylbenzoylmethyl)-4-nitroisothiazole Triethylamine (20.2 grams, 0.200 mol) was added to 200 ml of a tetrahydrofuran (THF) solution of 16.9 grams (0.100 mol) of 5-cyano-3-methyl-4-nitroisothiazole, and 74.6 grams (0.200 mol) of 4-dodecylsulfonylbenzoyl chloride was added dropwise. After heating under reflux for 8 hours, 200 ml of 1N aqueous sodium hydroxide solution was added dropwise. After heating under reflux for 3 hours, the reaction mixture was left to cool, poured into ice water and extracted with ethyl acetate. 5-Cyano-3-(4-dodecylsulfonylbenzoylmethyl)-4-nitroisothiazole (11.9 grams, 23.5 mmol) was obtained on refinement using silica gel column chromatography.

(1-2) Preparation of Coupler (1)

Reduced iron (19.5 grams, 0.35 mol) and 0.9 gram of ammonium chloride were dispersed in 12 ml of water and 100 ml of isopropyl alcohol and heated under reflux for 10 minutes. 5-Cyano-3-(4-dodecylsulfonylbenzoylmethyl)-4-nitroisothiazole (10.1 grams, 20.0 mmol) was then added in small quantities and, after heating under reflux for 3 hours, the mixture was subjected to usual work-up procedures. The crude product was dissolved in 50 ml of acetic acid and heated under reflux for 4 hours, after which it was worked-up using normal procedures. Coupler (1) (6.62 grams, 14.5 mmol) was obtained by refinement using silica gel column chromatography. Yield was 72.3%

The cyan dye which was obtained by the oxidative coupling of the above Coupler (1) with 2-methyl-4-(N-ethyl-N-methanesulfonylethylamino)aniline had a remarkably sharp absorbance when compared with the dyes obtained from conventional phenol couplers, and the cut-off on the short wavelength side was good.

Synthesis Example 2: (Synthesis of Coupler (33))

Preparation of 5-Acetylamino-3-methyl-4-nitroisothiazole

5-Acetylamino-3-methylisothiazole (46.8 grams, 0.300 mol) was added little by little with ice cooling to a mixed solution comprised of 28 ml of fuming nitric acid, 100 ml of fuming sulfuric acid and 300 ml of concentrated sulfuric acid. After stirring for 3 hours, the mixture was poured into ice water. The crystals which precipitated were recovered using suction filtration, washed with water and dried. Recovery was 34.4 grams (0.171 mol). Yield was 57.0%.

(2-2) Preparation of 5-Acetylamino-3-[bis-(4-chlorobenzoyl)methyl]-4-nitroisothiazole 5-Acetylamino-3-methyl-4-nitroisothiazole (10.1 grams, 50.0 mmol) and 11.1 grams of triethylamine were dissolved in 200 ml of acetonitrile, and 19.3 grams (0.110 mol) of 4-chlorobenzoyl chloride was dissolved in 100 ml of acetonitrile and added dropwise. After stirring for 4 hours, the mixture was poured into water and extracted with ethyl acetate. The extract was washed with aqueous bicarbonate and then with saturated salt water and dried over anhydrous sodium sulfate. After filtration, the solvent was distilled off under reduced pressure and the residue was refined using silica gel column chromatography. Recovery was 8.47 grams (17.7 mmol). Yield was 35.4%.

(2-3) Preparation of 5-Acetylamino-3-(4-chlorobenzoylethyl)-4-nitroisothiazole 5-Acetylamino-3-[bis-(4-chlorobenzoyl)methyl]-4-nitroisothiazole (3.88 grams, 8.01 mmol) was added to a mixture comprised of 100 ml of dimethylsulfoxide and 100 ml of 1M aqueous sodium hydroxide solution and the mixture was stirred for 10 minutes. The mixture was heated under reflux, then left to cool, poured into ice water and extracted with ethyl acetate, and the product was refined using silica gel column chromatography. Recovery was 2.36 grams (6.95 mmol). Yield was 86.8%.

(2-4) Preparation of Coupler (33)

Reduced iron (2.94 grams, 50.0 mmol) and 0.30 gram of ammonium chloride were introduced into 20 ml of isopropyl alcohol and 3 ml of water, and the mixture was heated under reflux for 20 minutes. 5-Acetylamino-3-(4-chlorobenzoylmethyl)-4-nitroisothiazole (2.04 grams, 6.00 mmol) was added little by little, and the mixture was heated under reflux for 2 hours. The iron was removed by suction filtration, water was added, and the mixture was extracted with ethyl acetate. The extract was washed with saturated salt water and then dried over anhydrous sodium sulfate. After filtration, the solvent was removed by distillation under reduced pressure. The residue was dissolved in 20 ml of acetic acid and heated under reflux for 2 hours. The mixture was then poured into water and extracted with ethyl acetate. The extract was washed with aqueous bicarbonate and then with saturated salt water, and dried over anhydrous sodium sulfate. After filtration, the solvent was removed by distillation and the material was crystallized from ethyl acetate. Recovery was 1.23 gram (4.22 mmol); Yield was 70.3%; and Melting Point was 210° C.

The magenta dye obtained by the oxidative coupling of the above-mentioned coupler (33) with 2-methyl-4-(N-ethyl-N-methanesulfonylamino)aniline had a remarkably sharp absorbance when compared with dyes originating from conventional magenta couplers, and the cut-off on the short wavelength side was good.

The absorption spectrum in ethyl acetate solution of the magenta dye obtained by the oxidative coupling of coupler (33) described above is shown in FIG. 1. The peak absorption wavelength was 521.1 nm.

The other dye forming couplers represented by formula (I) of the present invention (where X is a hydrogen atom, referred to herein as "four-equivalent couplers") can also be prepared using similar methods of synthesis to those described above.

Dye forming couplers in which X in formula (I) is a leaving group can be synthesized by introducing a leaving group using the method described below into four-equivalent couplers which have been obtained in this way.

There are four methods, as indicated below, of introducing a leaving group, depending on the type of leaving group which is to be introduced.

(1) When the Leaving Group is a Halogen Atom

The most general halogen atom is the chlorine atom, and it can be introduced by the chlorination of a four-equivalent coupler in which X in formula (I) is a hydrogen atom with, for example, sulfuryl chloride or chlorosuccinimide in a halogenated hydrocarbon solvent such as chloroform and methylene chloride.

(2) When the Leaving Group is Bonded via an Oxygen Atom

There is a first method where the coupling position of the four-equivalent coupler is halogenated and then reacted with a phenolic compound in the presence of a base, and a second method where a hydroxyl group at the coupling site of the four-equivalent coupler is reacted with an active halogen compound in the presence of a base.

(3) When the Leaving Group is Bonded via a Sulfur Atom

There is a first method where the four-equivalent coupler and a sulfenyl chloride which provides the leaving group are reacted in the presence or absence of a base, and a second method were a mercapto group is introduced into the coupling position of the four-equivalent coupler and a halide is reacted with this mercapto group.

(4) When the Leaving Group is Bonded via a Nitrogen Atom

There is a first method where a nitroso group is provided at the coupling site of the four-equivalent coupler using an appropriate nitrosating agent and this is reduced in an appropriate manner (e.g., by hydrogenation with a palladium/carbon catalyst or by means of a chemical reduction method using stannous chloride), after which the product is reacted with various halides. There is a second method where the coupling position of the four-equivalent coupler can be halogenated with an appropriate halogenating agent (e.g., sulfuryl chloride) and then substituted with a nitrogen containing heterocyclic ring using an appropriate base catalyst as disclosed in JP-B-56-45135. There is also a third method where a 10n-electron or 6n-electron-type nitrogen-containing heterocyclic ring is introduced into the halogenated coupler in the presence or absence of an aprotic polar solvent. (The term "JP-B" as used herein signifies an "examined Japanese patent publication".)

Reference can also be made to U.S. Pat. Nos. 3,894,875, 3,933,501, 4,296,199, 3,227,554, 3,476,563, 4,296,200, 4,234,678, 4,228,233, 4,351,897, 4,264,723, 4,366,237, 3,408,194, 3,725,067, 3,419,391 and 3,926,631; and JP-B-56-45135, JP-B-57-36577, JP-A-57-70871, JP-A-57-96343, JP-A-53-52423, JP-A-51-105820, JP-A-53-129035 and JP-A-54-48540, in connection with the above-mentioned methods for the introduction of leaving groups.

The reaction scheme for the formation of a dye from a coupler which is represented by formula (I) according to the present invention is indicated below.

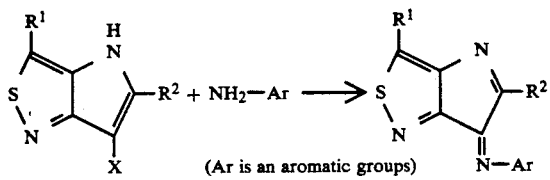

(Ar is an aromatic groups)

The couplers represented by formula (I) according to the present invention undergo a coupling reaction with the oxidized form of primary aromatic amine derivatives and form dyes. These dyas can be used as cyan or magenta dyes in various applications (e.g., in filters, paints, inks, for image and information recording purposes and as dyes for printing purposes).

In those cases where the couplers represented by formula (I) according to the present invention are used in a silver halide photosensitive material, there should be, on a support, at least one layer which contains such a coupler. The layers which contain such a coupler according to the present invention should be hydrophilic colloid layers which are established on a support. In general, a color photosensitive material can be constructed by establishing, in this order on a support, at least one blue-sensitive silver halide emulsion layer, at least one green-sensitive silver halide emulsion layer and at least one red-sensitive silver halide emulsion layer. But the layers may be arranged in a different order.

Furthermore, at least one of the aforementioned photosensitive emulsion layers can be replaced by an infrared photosensitive silver halide emulsion layer. Color reproduction with the subtractive color method can be achieved by including silver halide emulsions which are sensitive to the respective wavelength bands, and color couplers which form dyes having a complementary relationship with the actinic light in the photosensitive emulsion layers. However, constructions in which the color formed by the color coupler and the photosensitive emulsion layer do not have such a relationship, are also possible.

In those cases where couplers according to the present invention are used in a color photosensitive material, their use in the green-sensitive or red-sensitive silver halide emulsion layers is especially desirable.

The amount of coupler which is added to a photosensitive materials should range from $1 \times 10^{-3}$ mol to 1 mol, and preferably from $2 \times 10^{-3}$ mol to $3 \times 10^{-1}$ mol, per mol of silver halide.

Furthermore, in those cases where the coupler according to the present invention is soluble in a aqueous alkaline solution, it can be dissolved in an aqueous alkaline solution together with a developing agent and other additives, and used to form color images using a so-called external-type developer. In such a case the amount added is from 0.0005 to 0.05 mol, and preferably from 0.005 to 0.02 mol, per liter of color developer.

The couplers of the present invention can be introduced into photosensitive materials using various known methods of dispersion. A method where the couplers are dissolved in a high boiling point organic solvent (a low boiling point organic solvent can be used conjointly, as required), emulsified and dispersed in an aqueous gelatin solution to form an oil in water dispersion which is then added to the silver halide emulsion, is preferred.

Examples of high boiling point solvents which can be used in the oil in water dispersion method have been disclosed, for example, in U.S. Pat. No. 2,322,027. Furthermore, actual examples of the process and effect of the latex loading method and of latexes for loading purposes as a polymer dispersion method have been disclosed, for example, in U.S. Pat. No. 4,199,363, and West German Patent Applications (OLS) 2,541,274 and 2,541,230, JP-B-53-41091 and European Patent laid open 029104. Methods of dispersion by means of organic solvent soluble polymers have been disclosed in PTC International Patent WO88/00723.

Examples of high boiling point organic solvents which can be used in the aforementioned oil-in-water dispersion method include esters of phthalic acid such as dibutyl phthalate, dioctyl phthalate, dicyclohexyl phthalate, di-2-ethylhexyl phthalate, decylphthalate, bis(2,4-di-tertamylphenyl)isophthalate and bis(1,1-diethylpropyl)phthalate; esters of phosphoric acid or phosphonic acid such as diphenyl phosphate, triphenyl phosphate, tricresyl phosphate, 2-ethylhexyl diphenyl phosphate, dioctyl butyl phosphate, tricyclohexyl phosphate, tri-2-ethylhexyl phosphate, tridodecyl phosphate, and di-2-ethylhexyl phenyl phosphate; esters of benzoic acid such as 2-ethylhexyl benzoate, 2-ethylexyl-2',4'-dichlorobenzoate, dodecyl benzoate, and 2-ethylhexyl p-hydroxybenzoate; amides such as N,N-diethyldecanamide and N,N-diethyllaurylamide; alcohols such as isostearyl alcohol; fatty acid esters such as dibutoxyethyl succinate, di-2-ethylhexyl succinate, 2-hexyldecyl tetradecanoic acid, tributyl citrate, diethyl azelate, isostearyl lactate and trioctyl lactate; aniline derivatives such as N,N-dibutyl-2-butoxy-5-tertoctylaniline; chlorinated paraffins such as paraffins which have a chlorine content of from 10% to 80%; trimesic acid esters such as tributyl trimesate; dodecylbenzene di-isopropylnaphthalene, phenols such as 2,4-tert-amylphenol, 4-dodecyloxyphenol, 4-dodecyloxycarbonylphenol and 4-(4-dodecyloxyphenylsulfonyl)phenol; carboxylic acids such as 2-(2,4-di-tert-amylphenoxybutyric acid) and 2-ethoxyoctadecanoic acid; alkylphoshoric acids such as di-(2-ethylhexyl)phosphoric acid and diphenylphosphoric acid. Moreover, organic solvents having a boiling point at least 30° C. but not more than about 60° C. such as ethyl acetate, butyl acetate, ethyl propionate, methyl ethyl ketone, cyclohexanone, 2-ethoxyethyl acetate and dimethylformamide can be used conjointly as auxiliary solvents.

The so-called highly polar, high boiling point organic solvents from among those listed above are preferred for the couplers of the present invention. From among those, the amides are preferred. Suitable amide high boiling point organic solvents are disclosed in, for example, U.S. Pat. Nos. 2,322,027, 4,127,413 and 4,745,049, as well as in the literature cited above. From among those solvents, the high boiling point organic solvents which have a specific dielectric constant (measured at 25° C., 10 Hz) of not more than about 6.5, and preferably of from 5 to 6.5, are preferred.

The high boiling point organic solvent should be used in an amount of from 0 to 2.0 times the amount of coupler by weight, and preferably in an amount of from 0 to 1.0 times the amount of coupler by weight.

The couplers according to the present invention can be used, for example, in color papers, color reversal papers, direct positive color photosensitive materials, color negative films, color positive films and color reversal negative films. Their use in color photosensitive materials which have a reflective support (e.g., color papers and color reversal papers) is preferred.

The silver halide emulsions used in the present invention may be any halogen composition such as silver iodobromide, silver chloroidobromide, silver bromide, silver chlorobromide and silver chloride.

The preferred halogen composition differs according to the type of photosensitive material in which it is being used for example, silver chlorobromide emulsions are used primarily for color papers; silver iodobromide emulsions which contain from 0.5 to 30 mol % (and preferably from 2 to 25 mol%) of silver iodide are used for camera photosensitive materials such as color negative films and color positive films; and silver bromide and silver chlorobromide emulsions are used for direct positive color photosensitive materials. Furthermore, the use of so-called high silver chloride emulsions which have a high silver chloride content is preferred for photosensitive materials for color paper purposes which are suitable for rapid processing. The silver chloride content of a high silver chloride emulsion is preferably at least 90 mol %, and most desirably at least 95 mol %.

A structure which has a silver bromide local phase in the form of a layer or in some other form, as described hereinafter, within and/or at the surface of the silver halide grain, is desirable in high silver chloride emulsions. The halogen composition of the above mentioned local phase preferably has a silver bromide content of at least 10 mol %, and most desirably it has a silver bromide content in excess of 20 mol %. The local phase can be present within the grain, or at the edges and corners of the grain surface, or on the surface of the grain. In a preferred embodiment, the local phase is grown epitaxially on the corners of the grain.

The use of essentially silver iodide free silver chlorobromide or silver chloride is preferred in the present invention. Here, the term "essentially silver iodide free" signifies that the silver iodide content is not more than 1 mol %, and preferably not more than 0.2 mol %.

The halogen composition in the emulsion may differ from grain to grain, or it may be same from grain to grain, but the nature of the grains is readily made homogeneous when emulsions in which the halogen composition is the same from grain to grain are used. Furthermore, the halogen composition distribution within the grains of the silver halide emulsion may be such that the grains have a so-called uniform structure in which the composition is the same in all parts of the silver halide grain; or it may be such that the grains have a so-called laminated structure in which the core inside the silver halide grains has a different halogen composition from the shell (a single layer or a plurality of layers) which surrounds the core; or it may be such that the grains are of a structure which has parts having different halogen compositions which are not in the form of a layer within the grains or at the grain surface (when present at the grain surface, the structure is such that the parts which have a different composition are joined onto the edges or corners of the grains, or onto the surfaces of the grain). Grains which have any such halogen composition distribution can be selected appropriately for use. The use of either of the latter two types of grain structure is preferable to the use of grains which have a uniform halogen composition for obtaining higher photographic speeds. It is also preferred from the viewpoint of controlling the occurrence of pressure fogging. In those cases where the silver halide grains have a structure as described above, the boundaries between the parts which have different halogen compositions may be distinct boundaries; or there may be an indistinct boundary with the formation of mixed crystals due to the difference in composition; or there may be a positive continuous variation in the structure.

As used herein, the average grain size is taken to be the diameter of a circle which has an area equal to the projected area of the grain and the average grain size is taken to be the average of these values. According to the present invention the average grain size of the silver halide grains which are included in the silver halide emulsions is preferably from 0.1 $\mu$m to 2 $\mu$m, and most desirably from 0.15 $\mu$m to 1.5 $\mu$m. Furthermore, the grain size distribution is preferably that of a so-called monodispersion having the variation coefficient of not more than 20%, and preferably not more than 15%. The variation coefficient is the value obtained by dividing the standard deviation of the grain size distribution by the average grain size. The monodisperse emulsions are preferably blended and used in the same layer, or lamination coated, in order to achieve a wide latitude.

The form of the silver halide grains may be a regular crystalline form such as a cubic, tetradecahedral form or an octahedral form, an irregular crystalline form such as a spherical or plate-like form, or a form which is a composite of such regular and irregular crystalline forms. Furthermore, the grains may be tabular grains.

The silver halide emulsions may be so-called surface latent image type emulsions where a latent image is formed principally on the surface of the grains, or they may be so-called internal latent image type emulsions where a the latent image is formed principally within the grains.

The silver halide photographic emulsions which can be used in this present invention can be prepared, for example, by the methods disclosed in *Research Disclosure* (RD) No. 17643 (December, 1978) pages 22-23, "I. Emulsion Preparation and Types", and *Research Disclosure* No. 18716 (November 1979) page 648, by P. Glafkides in *Chimie et Physique Photographique*, published by Paul Montel, 1967, by G. F. Duffin in *Photographic Emulsion Chemistry*, published by Focal Press, 1966, and by V. L. Zelikman et al. in *Making and Coating Photographic Emulsions*, published by Focal Press, 1964.

The mono-dispersions disclosed, for example, in U.S. Pat. Nos. 3,574,628 and 3,655,394, and British Patent No. 1,413,748, are also desirable.

Tabular grains which have an aspect ratio of at least about 5 can be used in the present invention. Tabular grains can be prepared easily using the methods described, for example, by Gutoff in *Photographic Science and Engineering*, Volume 14, pages 248–257 (1970), and in U.S. Pat. Nos. 4,434,226, 4,414,310, 4,433,048 and 4,439,520, and British Patent No. 2,112,157.

The crystal structure may be uniform, or the interior and exterior parts of the grains may have different halogen compositions. The grains may also have a phase-like structure. Furthermore, silver halides which have different compositions may be joined with an epitaxial junction, or they may be joined with compounds other than silver halides, such as silver thiocyanate or lead oxide.

Furthermore, mixtures of grains having various crystalline forms can be used.

The silver halide emulsions should generally have been subjected to physical ripening, chemical ripening and spectral sensitization.

Various polyvalent metal ion impurities can be introduced into the silver halide emulsions during the course of emulsion grain formation or physical ripening. Examples of compounds which can be introduced include salts of cadmium, zinc, lead, copper and thallium for example, and salts and complex salts of iron, ruthenium, rhodium, palladium, osmium, iridium and platinum which are group VIII elements.

Additives which can be used in physical ripening, chemical ripening and spectral sensitization are disclosed in *Research Disclosure* No. 17643, ibid No. 18716 and ibid, No. 307105. The locations of these disclosures are summarized in the Table below. Known photographically useful additives which are useful in the invention are also disclosed in the three *Research Disclosures* referred to above. The locations of these disclosures are also indicated in the Table below.

performance due to formaldehyde gas. Examples are disclosed in U.S. Pat. Nos. 4,411,987 and 4,435,503.

Various color couplers can be used conjointly. Actual examples of suitable couplers are disclosed in the patents cited in the aforementioned *Research Disclosure* No. 17643, sections VII-C - G, and ibid, No. 307105, sections VII-C - G.

For example, those disclosed in U.S. Pat. Nos. 3,933,501, 4,022,620, 4,326,024, 4,401,752 and 4,248,961, JP-B-58-10739, British Patent Nos. 1,425,020 and 1,467,760, U.S. Pat. Nos. 3,973,968, 4,314,023 and 4,511,649, and European Patent Nos. 249,473A, are preferred as yellow couplers.

The couplers of the present invention can be used conjointly with yellow couplers having a peak absorption wavelength of the colored dye which is formed located on the short wavelength side, and an absorbance on the long wavelength side beyond 500 nm which falls sharply. Such yellow couplers are disclosed, for example, in JP-A-63-123047 and JP-A-1-173499.

5-Pyrazolone-based compounds and pyrazoloazole-based compounds are preferred as magenta couplers to be used conjointly in the present invention. Especially preferred are those disclosed, for example, in U.S. Pat. Nos. 4,310,619 and 4,351,897, European Patent No. 73,636, U.S. Pat. Nos. 3,061,432 and 3,725,067, *Research Disclosure* No. 24220 (June 1984), JP-A-60-33552, *Research Disclosure* No. 24230 (June 1984), JP-A-60-43659, JP-A-61-72238, JP-A-60-35730, JP-A-55-118034, JP-A-60-185951, U.S. Pat. Nos. 4,500,630, 4,540,654 and 4,556,630, and International Patent WO 88/04795.

Phenol-based and naphthol-based couplers are cyan couplers which can be used conjointly in the present invention. Preferred examples include those disclosed,

| Type of Additive | RD17643 (December 1978) | RD18716 (November 1979) | RD307105 (November 1989) |
|---|---|---|---|
| 1. Chemical Sensitizers | Page 23 | Page 648, right hand column | Page 866 |
| 2. Speed Increasing Agents | | Page 648, right hand column | |
| 3. Spectral Sensitizers, Supersensitizers | Pages 23–24 | Page 648, right hand column - page 649, right hand column | Pages 866–868 |
| 4. Bleaching Agents | Page 24 | Page 647, right hand column | Page 868 |
| 5. Antifoggants, Stabilizers | Pages 24–25 | Page 649, right hand column | Pages 868–870 |
| 6. Light Absorbers, Filter Dyes and Ultraviolet absorbers | Pages 25–26 | Page 649, right hand column - page 650, left hand column | Page 873 |
| 7. Anti-staining Agents | Page 25, right hand column | Page 650, left hand column - right hand column | Page 872 |
| 8. Dye Image Stabilizers | Page 25 | Page 650, left hand column | Page 872 |
| 9. Film Hardening Agents | Page 26 | Page 651, left hand column | Pages 874–875 |
| 10. Binders | Page 26 | Page 651, left hand column | Pages 873–874 |
| 11. Plasticizers, Lubricants | Page 27 | Page 650, right hand column | Page 876 |
| 12. Coating promotors Surfactants | Pages 26–27 | Page 650, right hand column | Pages 875–876 |
| 13. Antistatic agents | Page 27 | Page 650, right hand column | Pages 876–877 |
| 14. Matting Agents | | | Pages 878–879 |

Furthermore, it is desirable to add compounds which can react with and fix formaldehyde to the photosensitive material to prevent deterioration of photographic for example, in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Laid Open 3,329,729, European Patent Nos. 121,365A and 249,453A, U.S. Pat. Nos. 3,446,622, 4,333,999, 4,775,616, 4,451,559, 4,427,767, 4,690,889, 4,254,212 and 4,296,199, and JP-A-61-42658.

Colored couplers for correcting unwanted absorptions of colored dyes may be used. Preferred examples include those disclosed, for example, in section VII-G of *Research Disclosure* No. 17643, U.S. Pat. No. 4,163,670, JP-B-57-39413, U.S.Pat. Nos. 4,004,929 and 4,138,258, and British Patent 1,146,368. Furthermore, the use of couplers which correct unwanted absorption of colored dyes using fluorescent dyes which are released on coupling are desirable. Examples are disclosed in U.S. Pat. No. 4,774,181. Also desirable are couplers which have, as leaving groups, dye precursor groups which can form dyes on reaction with developing agents such as those disclosed in U.S. Pat. No. 4,777,120.

The couplers disclosed in U.S. Pat. No. 4,366,237, British Patent No. 2,125,570, European Patent No. 96,570 and West German Patent (laid open) No. 3,234,533 are preferred as couplers of which the colored dyes have a suitable degree of diffusibility.

Typical examples of polymerized dye forming couplers are disclosed, for example, in U.S. Pat. Nos. 3,451,820, 4,080,211, 4,367,282, 4,409,320 and 4,576,910, and British Patent No. 2,102,137.

Compounds which release photographically useful residual groups on coupling can be used in the present invention. DIR couplers which release development inhibitors such as those disclosed in the patents cited in section VII-F of the aforementioned *Research Disclosure* 17643, VP-A-57-151944, JP-A-57-154234, JP-A-60-184248, JP-A-63-37346 and U.S. Pat. Nos. 4,248,962 and 4,782,012 are preferred.

The couplers disclosed in British Patent Nos. 2,097,140 and 2,131,188, JP-A-59-157638 and JP-A-59-170840 are preferred as couplers which release nucleating agents or development accelerators in the form of the image during development.

Other couplers which can be used conjointly in a photosensitive material according to the present invention include competitive couplers such as those disclosed, for example, in U.S. Pat. No. 4,130,427; multiequivalent couplers such as those disclosed, for example in U.S. Pat. Nos. 4,283,472, 4,338,393 and 4,310,618; DIR redox compound-releasing couplers, DIR coupler-releasing couplers, DIR coupler-releasing redox compounds or DIR redox-releasing redox compounds such as those disclosed, for example, in JP-A-60-185950 and JP-A-62-24252; couplers which release dyes of which the color is restored after elimination such as those disclosed in European Patent No. 173,302A; bleach accelerator-releasing couplers such as those disclosed, for example, in *Research Disclosure* No. 11449, ibid, No. 24241 and JP-A-61-201247; the ligand-releasing couplers such as those disclosed, for example, in U.S. Pat. No. 4,553,477; leuco dye-releasing couplers such as those disclosed in JP-A-63-75747; and couplers which release fluorescent dyes such as those disclosed in U.S. Pat. No. 4,774,181.

The standard amount of conjointly used color couplers should fall within the range from 0.001 to 1 mol per mol of photosensitive silver halide, and preferably from 0.01 to 0.5 mol per mol of photosensitive silver halide in the case of the yellow couplers, from 0.003 to 0.3 mol per mol of photosensitive silver halide in the case of the magenta couplers and from 0.002 to 0.3 mol per mol of photosensitive silver halide in the case of the cyan couplers.

Conjointly used couplers can be introduced into the photosensitive material using various known methods of dispersion such as those described above.

Photosensitive materials of the present invention may contain anti-color fogging agents such as hydroquinone derivatives, aminophenol derivatives, gallic acid derivatives and ascorbic acid derivatives.

Various anti-color fading agents can also be used in a photosensitive material according to the present invention. Hydroquinones, 6-hydroxychromans, 5-hydroxycoumarans, spirochromans, p-alkoxyphenols, hindered phenols centering on bisphenols, gallic acid derivatives, methylenedioxybenzenes, aminophenols, hindered amines, and ether and ester derivatives in which phenolic hydroxyl groups of the compounds have been silylated or alkylated, are typical organic anti-fading agents which can be used for the cyan, magenta and/or yellow images. Furthermore, metal complexes such as (bissalicylaldoximato) nickel and (bis-N,N-dialkyldithiocarbamato) nickel complexes, for example, can also be used for that purpose.

Actual examples of organic anti-color fading agents include the hydroquinones disclosed in U.S. Pat. Nos. 2,360,290, 2,418,613, 2,700,453, 2,701,197, 2,728,659, 2,732,300, 2,735,765, 3,982,944 and 4,430,425, British Patent No. 1,363,921 and U.S. Pat. Nos. 2,710,801 and 2,816,028; the 6-hydroxychromans, 5-hydroxychromans and spirochromans disclosed in U.S. Pat. Nos. 3,432,300, 3,573,050, 3,574,627, 3,698,909 and 3,764,337, and JP-A-52-152225; the spiroindanes disclosed in U.S. Pat. No. 4,360,589; the p-alkoxyphenols disclosed in U.S. Pat. No. 2,735,765, British Patent No. 2,066,975, JP-A-59-10539 and JP-B-57-19765; the hindered phenols disclosed in U.S. Pat. Nos. 3,700,455 and 4,228,235, JP-A-52-72224 and JP-B-52-6623; the gallic acid derivatives disclosed in U.S. Pat. No. 3,457,079; the methylenedioxybenzenes disclosed in U.S. Pat. No. 4,332,886; the aminophenols disclosed in JP-B-56-21144; the hindered amines disclosed in U.S. Pat. Nos. 3,336,135 and 4,268,593, British Patent Nos. 1,326,889, 1,354,313 and 1,410,846, JP-B-51-1420, JP-A-58-114036, JP-A-59-53846 and JP-A-59-78344; and the metal complexes disclosed in U.S. Pat. Nos. 4,050,938 and 4,241,155, and British Patent No. 2,027,731(A). The objective can be realized by adding these compounds to the photosensitive layer after co-emulsification with the corresponding color coupler; generally in an amount of from 5 to 100 wt % with respect to the coupler.

An introduction of ultraviolet absorbers into the cyan color forming layer and the layers on both sides adjacent thereto is effective for preventing deterioration of the cyan dye image due to heat and, more especially, due to light.

For example, benzotriazole compounds substituted with aryl groups such as those disclosed in U.S. Pat. No. 3,533,794, 4-thiazolidone compounds such as those disclosed in U.S Pat. Nos. 3,314,794 and 3,352,681, benzophenone compounds such as those disclosed in JP-A-46-2784, cinnamic acid ester compounds such as those disclosed in U.S. Pat. Nos. 3,705,805 and 3,707,395, butadiene compounds such as those disclosed in U.S. Pat. No. 4,045,229, or benzoxazole compounds such as those disclosed in U.S. Pat. Nos. 3,406,070 and 4,271,307 can be used as ultraviolet absorbers. Ultraviolet absorbing couplers such as α-naphthol based cyan dye forming couplers, and ultraviolet absorbing polymers can also be used. The ultraviolet absorbers may be mordanted in a specified layer.

From the above compounds, the aforementioned benzotriazole compounds which are substituted with aryl groups are preferred.

The use of gelatin as the binding agent or protective colloid in the emulsion layers of a photosensitive material according to the present invention is convenient, but other hydrophilic colloids, either alone or in conjunction with gelatin, can be used as well.

The gelatin may be a lime-treated gelatin, or it may be a gelatin which has been treated using acids. Details regarding the preparation of gelatins are disclosed by Arthur Weise in *The Macromolecular Chemistry of Gelatin* (published by Academic Press, 1964).

The addition of various fungicides and biocides to the photosensitive material according to the present invention is desirable. Examples include 1,2-benzisothiazolin-3-one, n-butyl p-hydroxybenzoate, phenol, 4-chloro-3,5-dimethylphenol, 2-phenoxyethanol and 2-(4-thiazolyl)benzimidazole. See, e.g., JP-A-63-257747, JP-A-62-272248 and JP-A 1-80941.

Where the photosensitive material according to the present invention is a direct positive color photosensitive material, nucleating agents such as hydrazine compounds and quaternary heterocyclic compounds or nucleation accelerators enhancing the effect of the nucleating agents disclosed, for example, in *Research Disclosure* No. 22534 (January 1983) can be used.

Transparent films such as cellulose nitrate films and poly(ethylene terephthalate) films, and reflective supports which are generally used in photographic photosensitive materials can be used as the supports according to the present invention. The use of a reflective support is preferred, particularly in view of the objectives of the invention.

The "reflective supports" which are preferably used according to the present invention have a high reflectivity, and the dye image which is formed in the silver halide emulsion layer is bright. Supports which have been covered with a hydrophobic resin containing a dispersion of a light reflecting material, such as titanium oxide, zinc oxide, calcium carbonate or calcium sulfate, and supports comprising a hydrophobic resin containing a dispersion of a light reflecting substance, are included as examples of such reflective supports. Use can be made of baryta paper, polyethylene coated paper, polypropylene based synthetic paper and transparent supports (e.g., glass plates, polyester films such as poly(ethylene terephthalate), cellulose triacetate or cellulose nitrate films, polyamide films, polycarbonate films, polystyrene films and poly(vinyl chloride) resins) on which a reflecting layer has been established or in which a reflective substance has been used conjointly.

Photosensitive materials according to the invention can be developed and processed using methods such as the general methods disclosed in the aforementioned *Research Disclosure* No. 17643, pages 28-29, and *Research Disclosure* No. 18716, left hand-right hand columns on page 615. For example, they can be subjected to color development, desilvering and water washing for color development processing. In the case of a reversal development process, they can be subjected to a black and white development, a water wash or rinsing, a reversal process and color development. In the desilvering process, bleach-fixing in which a bleach-fixer is used can be carried out rather than bleaching where a bleach is used and fixing where a fixer is used; and a combination of bleaching, fixing and a bleach-fixing process, in any order, can be used. A stabilization process may be carried out rather than water washing, or a stabilization process can be carried out after water washing. Furthermore, mono-bath processing where a single bath development, bleaching and fixing processing liquid is used can be carried out for achieving color development, bleaching and fixing with a single bath. Film prehardening processes, neutralization processes, stop fixing processes, film posthardening processes, conditioning processes and intensification processes, for example, may be used in combination with these processes. Intermediate water washing processes may also be used optionally, between the aforementioned processes. A so-called activator process can also be used in place of color development in these processing operations.

The color developer which is used is preferably an aqueous alkaline solution containing a primary aromatic amine derivative as a color developing agent. Aminophenol-based compounds are also useful as color developing agents, but the use of p-phenylenediamine-based compounds is preferred. Typical examples include 3-methyl-4-amino-N,N-diethylaniline, 3-methyl-4-amino-N-ethyl-N-$\beta$-hydroxyethylaniline, 4-amino-N-ethyl-N-$\beta$-hydroxyethylaniline, 3-methyl-4-amino-N-ethyl-N-$\beta$-methanesulfonamidoethylaniline, 3-methyl-4-amino-N-ethyl-$\beta$-methoxyethylaniline, and the sulfate, hydrochloride and p-toluenesulfonate salts of these compounds. Two or more of the above compounds can be used conjointly, depending on the intended purpose.

The color developer will generally contain pH buffers such as alkali metal carbonates, borates or phosphates, and development inhibitors or antifoggants such as chlorides, bromides, iodides, benzimidazoles, benzothiazoles or mercapto compounds. It may also contain, as required, various preservatives such as hydroxylamine, diethylhydroxylamine, sulfite, hydrazines such as N,N-biscarboxymethylhydrazine, phenylsemicarbazides, triethanolamine and catecholsulfonic acids; organic solvents such as ethylene glycol and diethylene glycol; development accelerators such as benzyl alcohol, polyethylene glycol, quaternary ammonium salts and amines; dye forming couplers; competitive couplers; auxiliary developing agents such as 1-phenyl-3-pyrazolidone; nucleating agents such as sodium borohydride and hydrazine based compounds; thickeners; various chelating agents such as ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid) and salts thereof; fluorescent whiteners such as 4,4'-diamino-2,2'-disulfostilbene-based compounds; and various surfactants such as alkylsulfonic acids, arylsulfonic acids, aliphatic carboxylic acids or aromatic sulfonic acids.

The use of an essentially benzyl alcohol free color developer is preferred in the present invention. An "essentially benzyl alcohol free" color developer is a developer which contains not more than 2 ml/liter, preferably not more than 0.5 ml/liter of benzyl alcohol, and most preferably contains no benzyl alcohol at all.

The color developers used in the present invention preferably are essentially sulfite ion free. The term "essentially sulfite ion free" as used herein signifies a preferred sulfite ion concentration of not more than $3.0\times10^{-3}$ mol/liter, and most desirably that no sulfite ion is present.

The color developers used in the present invention preferably are essentially hydroxylamine free. The term "essentially hydroxylamine free" as used herein signifies a preferred hydroxylamine concentration of not more than $5.0\times10^{-3}$ mol/liter, and most desirably that no hydroxylamine present. The inclusion of organic preservatives other that hydroxylamine (e.g., hydroxylamine derivatives and hydrazine derivatives) in the color developer is preferred.

The pH of the color developer is generally from 9 to 12.

Furthermore, black and white development, a water wash or rinse, reversal processing and color development processing are generally carried out in a color reversal development process. A reversal bath which contains a fogging agent, or a light reversal process, can be used for the reversal process. Furthermore, the above-mentioned fogging agent may be included in the color developer; thereby the reversal process can then be omitted.

Black and white developers useful in black and white development processing are those known generally for photographic processing of black and white photographic photosensitive materials. Various additives which can generally be added to black and white developers can be included.

Typical additives include developing agents such as 1-phenyl-3-pyrazolidone, N-methyl-p-aminophenol and hydroquinone; preservatives such as sulfite; pH buffers comprised of water soluble acids such as acetic acid and boric acid; pH buffers or development accelerators comprised of alkalies such as sodium hydroxide, sodium carbonate and potassium carbonate; inorganic or organic development inhibitors such as potassium bromide, 2-methylbenzimidazole and methylbenzthiazole; hard water softening agents such as ethylenediaminetetraacetic acid and polyphosphoric acid salts; antioxidants such as ascorbic acid and diethanolamine; organic solvents such as triethyleneglycol and cellosolve; and anti-surface super-development agents such as trace amounts of iodide and mercapto compounds.

Prevention of evaporation and aerial oxidation of the liquid by reducing the area of contact with the air in the processing tank is desirable in those cases where the replenishment rate of developers has been reduced. The methods in which a shielding material such as a floating lid is established on the surface of the processing liquid in the processing tank can be used for minimizing the contact area with the air in the processing tank. This technique is preferably applied not only with both the color development tank and the black and white development tank, but to all of the subsequent processing steps as well. Furthermore, the replenishment rate can be reduced by suppressing the accumulation of bromide ion in the developer. An example is the use of a regeneration means.

Color development processing time is generally set between 2 and 5 minutes, but shorter processing times can be achieved by using higher temperatures and pH levels, and by using higher concentrations of color developing agent.

The color developed photographic emulsion layer is subjected to a desilvering process. The desilvering process may be such that bleaching and fixing are carried out separately, or bleaching and fixing can be carried out simultaneously (e.g., in a bleach-fix process). Moreover, bleach-fixing can be carried out after bleaching to speed up processing. Furthermore, processing can be carried out in two consecutive bleach-fix baths, fixing can be carried out prior to bleach-fixing, or bleaching may be carried out after bleach-fixing, depending on the objective of processing. In the present invention, the effect of the invention is pronounced when bleach fixing is carried out immediately after color development.

Compounds of multi-valent metals, such as iron(III), peracids, quinones, and iron salts, for example, can be used as bleaching agents in the bleach and bleach-fix baths. Thus, iron chloride, ferricyanide; dichromates; organic complex salts of iron(III) such as metal complex salts with aminopolycarboxylic acids (e.g., ethylenediaminetetraacetic acid, diethylenetriaminepentaacetic acid, 1,3-diaminopropanetetraacetic acid); and persulfates, can be used as typical bleaching agents. From among the above materials, it is preferred to use aminopolycarboxylic acid iron(III) complex salts. Moreover, the aminopolycarboxylic acid iron(III) complex salts are especially useful in both bleach baths and bleach-fix baths. The bleach baths and bleach-fix baths in which aminopolycarboxylic acid iron(III) complex salts are used are generally used at a pH of from 3.5 to 8.

Known additives including rehalogenating agents such as ammonium bromide and ammonium chloride; pH buffers such as ammonium nitrate; and metal corrosion inhibitors such as ammonium sulfate, can be added to the bleach and bleach-fix baths.

In addition to the compounds mentioned above, the inclusion of organic acids in the bleach and bleach fix baths is desirable for preventing the occurrence of bleach staining. The most desirable organic acids are compounds which have an acid dissociation constant (pKa) of from 2 to 5.5. Preferred examples of such compounds include acetic acid and propionic acid.

Thiosulfate, thiocyanate, thioether based compounds, thioureas and large amounts of iodide can be used, for example, as the fixing agents which are used in fixers and bleach-fixers. However, thiosulfates are generally used, and ammonium thiosulfate can be used in the widest range of applications. Furthermore, the conjoint use of a thiocyanate, thioether based compounds and thiourea, with thiosulfate is also desirable.

Sulfite, bisulfite, carbonyl/bisulfite addition compounds, and the sulfinic acid compounds disclosed in European Patent 294,769A are preferred preservatives for fixers and bleach-fixers. Moreover, the addition of various aminopolycarboxylic acids and organic phosphonic acids such as 1-hydroxyethylidene-1,1-diphosphonic acid, N,N,N',N'-ethylenediaminetetraphosphonic acid to the fixers and bleach-fixers is desirable for stabilization of the bath.

Various fluorescent whiteners, anti-foaming agents; surfactants; polyvinylpyrrolidone and methanol, can also be included in the fixers and bleach fixers.

Bleaching accelerators can be added, as required, to bleach baths, bleach-fix baths or bleach or bleach-fix prebaths. Actual examples of useful bleach accelerators include compounds having a mercapto group or a disulfide group such as those disclosed in U.S. Pat. No. 3,893,858, West German Patent Nos. 1,290,812 and 2,059,988, JP-A-53-32736, JP-A-53-57831, JP-A-53-37418, JP-A-53-72623, JP-A-53-95630 JP-A-53-95631, JP-A-53-104232, JP-A-53-124424, JP-A-53-141623, JP-A-53-28426, and Research Disclosure No. 17129 (July 1978); thiazolidine derivatives such as those disclosed in JP-A-50-140129; thiourea derivatives such as those disclosed in JP-B-45-8506, JP-A-52-20832, JP-A-53-32735 and U.S. Pat. No. 3,706,561; iodides such as those disclosed in West German Patent No. 1,127,715 and JP-A-58-16235; polyoxyethylene compounds such as those disclosed in West German Patent Nos. 966,410 and 2,748,430; polyamide compounds such as those disclosed in JP-B-45-8836; other compounds such as those disclosed in JP-A-49-42434, JP-A-49-59644, JP-A-53-94927, JP-A-54-35727, JP-A-55-26506 and JP-A-58-163940; and bromide ion. From among the above compounds, those which have a mercapto group or a disulfide group are preferred due to their large accelerating effect, and the compounds disclosed in U.S. Pat. No. 3,893,858, West German Patent No. 1,290,812 and JP-A-53-95630 are especially desirable. Moreover, the compounds disclosed in U.S. Pat. No. 4,552,834 are also desirable. These bleach accelerators may also be added to the photosensitive material. Such bleaching accelerators are especially effective when bleach-fixing camera color photosensitive materials.

The total desilvering process time is preferably short and within the range where desilvering failure does not occur. The preferred time is from 1 to 3 minutes. Furthermore, the processing temperature is from 25° C. to 50° C., and preferably from 35° C. to 45° C.

Agitation, strongly as possible, is desirable in the desilvering process. Actual methods for strong agitation include those in which the processing liquid is forced as a jet onto the emulsion surface of the photosensitive material. See JP-A-62-183460. Such methods of strong agitation are effective in bleach baths, bleach-fix baths and fixing baths.

The color photosensitive material of the present invention is generally subjected to water washing after desilvering. Stabilization may be carried out rather than water washing. Known methods such as those disclosed in JP-A-57-8543, JP-A-58-14834 and JP-A-60-220345 can all be used for such stabilization. Furthermore, a water washing process -stabilization process in which a stabilizing bath is used as a final bath containing a dye stabilizing agent and surfactant as typical of processing camera color photosensitive materials, can also be employed.

Hard water softening agents such as inorganic phosphoric acid, polyaminocarboxylic acids and organic aminophosphonic acids; isothiazolone compounds and thiabendazoles, and chlorine-based biocides such as chlorinated sodium isocyanurate; metal salts such as Mg salts, Al salts and Bi salts; surfactants; film hardening agents; and biocides, for example, can be included in the washing water or stabilizer.

The amount of wash water used in the water washing process can be fixed within a wide range, depending on the characteristics (e.g., the materials such as couplers used therein) and application of the photosensitive material, the wash water temperature, the number of water washing tanks (number of water washing stages), the replenishment system (i.e. whether a counter-flow or a sequential flow system is used), and various other factors. The relationship between the amount of water used and the number of washing tanks in a multi-stage counter-flow system can be obtained using the method outlined on pages 248–253 of the *Journal of the Society of Motion Picture and Television Engineers*, Vol. 64 (May 1955). Furthermore, the method for reducing calcium ion and magnesium ion concentrations disclosed in JP-A-62-288838 can be used very effectively.

The pH of the wash water should be from 4 to 9, preferably from 5 to 8. The washing water temperature and the washing time can vary depending on the characteristics and application of the photosensitive material. In general, however, washing conditions of from 20 seconds to 10 minutes at a temperature of from 15° C. to 45° C., and preferably of from 30 seconds to 5 minutes at a temperature of from 25° C. to 40° C., should be used.

Dye stabilizing agents which can be used in the stabilizer include aldehydes such as formalin and glutaraldehyde, N-methylol compounds such as dimethylolurea, hexamethylenetetramine and aldehyde/bisulfite addition compounds, for example. Furthermore, pH controlling buffers such as boric acid and sodium hydroxide; chelating agents such as 1-hydroxyethylidene-1,1-diphosphonic acid and ethylenediaminetetraacetic acid; agents for preventing the occurrence of sulfiding such as alkanolamines; fluorescent whiteners; and fungicides, for example, can also be included in the stabilizer.

The overflow which accompanies replenishment of the above mentioned water washing and/or stabilizing baths can be reused in other processes such as desilvering.

Color developing agents may be incorporated into the photosensitive material of the present invention to simplify and speed up processing. The incorporation of various color developing agent precursors is preferred. Examples of such include the indoaniline-based compounds disclosed in U.S. Pat. No. 3,342,597, the Shiff's base-type compounds disclosed in U.S. Pat. No. 3,342,599, *Research Disclosure* No. 14850 and ibid No. 15159, the aldol compounds disclosed in *Research Disclosure* No. 13924, the metal complex salts disclosed in U.S. Pat. No. 3,719,492 and the urethane-based compounds disclosed in JP-A-53-135628.

Various 1-phenyl-3-pyrazolidones may be incorporated, as required, into the photosensitive material of the present invention to accelerate color development. Typical compounds are disclosed, for example, in JP-A-56-64339, JP-A-57-144547 and JP-A-58-115438.

The various processing baths should be used at temperatures of from 10° C. to 50° C. The standard temperature is generally from 33° C. to 38° C., but accelerated processing and shorter processing times can be realized at higher temperatures. On the other hand, however, increased picture quality and improved processing bath stability can be achieved at lower temperatures.

In the interest of brevity and conciseness, the contents of the aforementioned numerous patents and articles are hereby incorporated by reference.

The invention is described in further detail using of illustrative examples, but the invention is not to be construed as being limited in any way by these examples.

EXAMPLE 1

Preparation of Sample 101

Sample 101 of a layer structure indicated below was prepared on a cellulose triacetate film base. The coating liquid for the first layer was prepared in the following way.

Preparation of the First Layer Coating Liquid

Cyan coupler (A-1) (1.01 grams) and 2.0 grams of dibutyl phthalate were added to 10.00 cc of ethyl acetate to form a complete solution. The ethyl acetate coupler solution was added to 42 grams of a 10% aqueous gelatin solution (which contained 5 grams/liter of sodium dodecylbenzenesulfonate) and the mixture was emulsified and dispersed with a homogenizer. After emulsification and dispersion, the total weight was made up to 100 grams using distilled water. This emulsified dispersion (100 grams) was mixed with 8.2 grams of a high silver chloride emulsion (silver bromide content 0.5 mol %) and the first layer coating liquid was prepared in such a way to provide the composition indicated below. 1-Hydroxy-3,5-dichloro-s-triazine, sodium salt, was used as a gelatin film hardening agent.

The layer structure of each layer is indicated below.

Support

Cellulose triacetate film

| First Layer (Emulsion Layer) | |
|---|---|
| High silver chloride emulsion | as silver 0.32 g/m$^2$ |
| Gelatin | 2.70 g/m$^2$ |
| Cyan coupler (A-1) | 0.49 g/m$^2$ |
| Dibutyl phthalate | 0.98 g/m$^2$ |
| Second layer (Protective Layer) | 1.70 g/m$^2$ |
| Gelatin | |

Cyan Coupler (A-1)

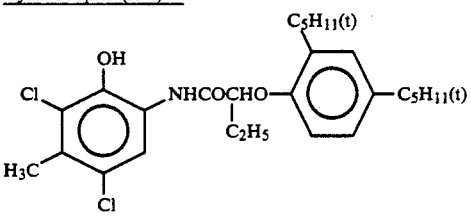

Preparation of Samples 102–106

These samples were prepared in the same way as sample 101 except that equimolar amounts of the couplers shown in Table 1 were used rather than cyan coupler (A-1).

Evaluation of Hue

Samples 101 to 106 were subjected to a step-wedge exposure using white light and then developed and processed using the processing operations indicated below.

After processing, spectral absorption measurements were made in the maximum density portion and the hue was evaluated on the basis of the extent of side absorptions and the extent of the cut-off on the short wavelength side using the equation below.

Extent of Side Absorption =

$$\frac{\text{Absorption Density at 410 nm}}{\text{Absorption Density at Peak Absorption Wavelength}}$$

Extent of Cut-off on Short Wavelength Side =

$$\frac{\text{Absorption Density at 535 nm}}{\text{Absorption Density at Peak Absorption Wavelength}}$$

The results are set forth in Table 1.

Evaluation of Image Fastness

Samples 101 to 106 were also subjected to a wedge exposure using white light and then developed and processed using the processing operations indicated below.

The developed and processed samples were left to stand for 10 days at 85° C., and a fading test was carried out. The cyan density ($D_R$) after the fading test at the point where the cyan density before the fading test was 1.5, was measured and the image fastness of each sample was evaluated using the value obtained using the equation indicated below (the dye survival factor)

Dye Survival Factor = $\{(D_R)/1.5\} \times 100$

The results are set forth in Table 1.

| Processing Operation | Temperature | Time |
|---|---|---|
| Color Development | 38° C. | 45 seconds |
| Bleach-fixing | 35° C. | 45 seconds |
| Rinse (1) | 35° C. | 30 seconds |
| Rinse (2) | 35° C. | 30 seconds |
| Rinse (3) | 35° C. | 30 seconds |
| Drying | 80° C. | 60 seconds |

(A three-tank counter flow system from rinse (3) to rinse (1) was used)

The composition of each processing bath is set forth below.

| Color Developer | |
|---|---|
| Water | 800 ml |
| Ethylenediamine-N,N,N,N-tetramethylene- phosphonic acid | 3.0 grams |
| Triethanolamine | 8.0 grams |
| Potassium chloride | 3.1 grams |
| Potassium bromide | 0.015 gram |
| Potassium carbonate | 25 grams |
| Hydrazino di-acetic acid | 5.0 grams |
| N-Ethyl-N-($\beta$-methanesulfonamidoethyl)-3- methyl-4-aminoaniline sulfate | 5.0 grams |
| Fluorescent whitener (WHITEX-4, made by Sumitomo Chemicals) | 2.0 grams |
| Water to make | 1000 ml |
| pH (potassium hydroxide added) | 10.05 |
| Bleach-fixer | |
| Water | 400 ml |
| Aqueous ammonium thiosulfate solution (700 grams/liter) | 100 ml |
| Ammonium sulfite | 45 grams |
| Ethylenediaminetetraacetic acid, iron (III) ammonium salt | 55 grams |
| Ethylenediaminetetraacetic acid | 3 grams |
| Ammonium bromide | 30 grams |
| Nitric acid (67%) | 27 grams |
| Water to make | 1000 ml |
| pH | 6.3 |

Rinse Bath

Ion exchanged water (calcium and magnesium both not more than 3 ppm)

TABLE 1

| Sample No. | Coupler | Extent of Side Absorption | Cut-off on Short Wavelength Side | Heat Fastness | Remarks |
|---|---|---|---|---|---|
| 101 | A-1 | 0.234 | 0.192 | 78% | Comparison |
| 102 | Illustrative coupler (1) | 0.101 | 0.151 | 90% | Invention |
| 103 | Illustrative coupler (2) | 0.100 | 0.149 | 89% | Invention |
| 104 | Illustrative coupler (24) | 0.092 | 0.121 | 94% | Invention |
| 105 | Illustrative coupler (31) | 0.093 | 0.120 | 91% | Invention |

TABLE 1-continued

| Sample No. | Coupler | Extent of Side Absorption | Cut-off on Short Wavelength Side | Heat Fastness | Remarks |
|---|---|---|---|---|---|
| 106 | Illustrative coupler (32) | 0.091 | 0.122 | 90% | Invention |

As may be seen from Table 1, the samples using a coupler according to this invention formed dyes which had little side absorbance, and provided a good cut-off on the short wavelength side. Moreover, the heat fastness of the dyes which were formed was excellent.

EXAMPLE 2

Samples were prepared in the same way as in Example 1, except that a silver iodobromide emulsion (7.0 mol % silver iodide) was used rather than the high silver chloride emulsion used in Example 1. The samples prepared in this way were developed and processed using the processing operations indicated below, and evaluated in the same way as the samples of Example 1. The samples obtained by replacing the emulsions of Samples 101 to 106 in Example 1 were Samples 201 to 206, respectively.

The results were equivalent to those of Example 1; i.e., the dyes formed from the couplers according to the present invention had a small side absorption and a good cutoff on the short wavelength side in a silver iodobromide based photosensitive material.

Furthermore, the dyes which were formed had good heat fastness.

| Process | Processing Time | Processing Temperature |
|---|---|---|
| Color development | 3 minutes 15 seconds | 38° C. |
| Bleaching | 1 minute 00 second | 38° C. |
| Bleach-fixing | 3 minutes 15 seconds | 38° C. |
| Water Wash (1) | 40 seconds | 35° C. |
| Water Wash (2) | 1 minute 00 second | 35° C. |
| Stabilization | 40 seconds | 38° C. |
| Drying | 12 minutes 15 seconds | 55° C. |

The composition of each processing bath is indicated below.

| | Units: Grams |
|---|---|
| Color Developer | |
| Diethylenetriaminepentaacetic acid | 1.0 |
| 1-Hydroxyethylidene-1,1-diphosphonic acid | 3.0 |
| Sodium sulfite | 4.0 |
| Potassium carbonate | 30.0 |
| Potassium bromide | 1.4 |
| Potassium iodide | 1.5 mg |
| Hydroxylamine sulfate | 2.4 |
| 4-[N-ethyl-N-β-hydroxyethylamino]-2-methylaniline sulfate | 4.5 grams |
| Water to make | 1.0 liter |
| pH | 10.05 |
| Bleach | |
| Ethylenediaminetetraacetic acid, ferric ammonium salt, dihydrate | 120.0 |
| Ethylenediaminetetraacetic acid, di-sodium salt | 10.0 |
| Ammonium bromide | 100.0 |
| Ammonium nitrate | 10.0 |
| Bleach accelerator | 0.005 mol |

$$\left[\left(\begin{array}{c}H_3C\\ \\H_3C\end{array}\right\!\!N-CH_2-CH_2-S\right)_2\right].2HCl$$

| | Units: Grams |
|---|---|
| Aqueous ammonia (27%) | 15.0 ml |
| Water to make | 1.0 liter |
| pH | 6.3 |
| Bleach-fixer | |
| Ethylenediaminetetraacetic acid, ferric ammonium salt, dihydrate | 50.0 |
| Ethylenediaminetetraacetic acid, di-sodium salt | 5.0 |
| Sodium sulfite | 12.0 |
| Aqueous ammonium thiosulfate solution (700 grams/liter) | 240.0 ml |
| Aqueous ammonia (27%) | 6.0 ml |
| Water to make | 1 liter |
| pH | 7.2 |

Water Washing Water

Town water was passed through a mixed bed type column which had been packed with an H-type strongly acidic cation exchange resin ("Amberlite IR-120B", made by the Rohm and Hass Co.) and an OH-type strongly basic anion exchange resin ("Amberlite IRA-400", made by the same company) and treated in such a way that the calcium and magnesium ion concentrations were not more than 3 mg/liter, after which 20 mg/liter of sodium isocyanurate dichloride and 0.15 g/liter of sodium sulfate were added. The pH of this liquid was within the range from 6.5 to 7.5.

| Stabilizer | Units: Grams |
|---|---|
| Formalin (37%) | 2.0 ml |
| Polyoxyethylene p-monononylphenyl ether (average degree of polymerization 10) | 0.3 |
| Ethylenediamine tetra-acetic acid, di-sodium salt | 0.05 |
| Water to make | 1.0 liter |
| pH | 5.0–8.0 |

EXAMPLE 3

Tests and evaluations were carried out in the same manner as in Example 2, except that the processing operations described below were used.

The results obtained are set forth in Table 2.

| | Processing Operations | |
|---|---|---|
| Process | Time | Temperature |
| First development | 6 minutes | 38° C. |
| Water wash | 2 minutes | 38° C. |
| Reversal | 2 minutes | 38° C. |
| Color development | 6 minutes | 38° C. |
| Conditioning | 2 minutes | 38° C. |
| Bleaching | 6 minutes | 38° C. |
| Fixing | 4 minutes | 38° C. |
| Water washing | 4 minutes | 38° C. |
| Stabilization | 1 minute | 38° C. |
| Drying | | |

The compositions of the processing baths were as indicated below.

| First Developer | |
|---|---|
| Water | 700 ml |
| Nitrilo-N,N,N-trimethylenephosphonic acid, pentasodium salt | 2 grams |
| Sodium sulfite | 20 grams |
| Hydroquinone monosulfonic acid | 30 grams |
| Potassium carbonate (monohydrate) | 30 grams |
| 1-Phenyl-4-methyl-4-hydroxymethyl-3-pyrazolidone | 2 grams |
| Sodium bromide | 2.5 grams |
| Potassium thiocyanate | 1.2 grams |
| Potassium iodide (0.1% solution) | 2 ml |
| Water to make | 1000 ml |
| pH | 9.60 |
| Reversal Bath | |
| Water | 700 ml |
| Nitrilo-N,N,N-trimethylenephosphonic acid, pentasodium salt | 3 grams |
| Stannous chloride (dihydrate) | 1 gram |
| p-Aminophenol | 0.1 gram |
| Sodium hydroxide | 8 grams |
| Glacial acetic acid | 15 mg |
| Water to make | 1000 ml |
| pH | 6.00 |
| Color Developer | |
| Water | 700 ml |
| Nitrilo-N,N,N-trimethylenephosphonic acid, pentasodium salt | 3 grams |
| Sodium sulfite | 7 grams |
| Trisodium phosphate (dodecahydrate) | 36 grams |
| Potassium bromide | 1 gram |
| Potassium iodide (0.1% solution) | 90 ml |
| Sodium hydroxide | 3 grams |
| Citrazinic acid | 1.5 grams |
| N-Ethyl-N-(β-methanesulfonamidoethyl)-3-methyl-4-aminoaniline sulfate | 11 grams |
| 3,6-Dithiaoctane-1,8-diol | 1 gram |
| Water to make | 1000 ml |
| pH | 11.80 |
| Conditioner | |
| Water | 700 ml |
| Sodium sulfite | 12 grams |
| Ethylenediaminetetraacetic acid, disodium salt, dihydrate | 8 grams |
| Thioglycerine | 0.4 ml |
| Glacial acetic acid | 3 ml |
| Water to make | 1000 ml |
| pH | 6.60 |
| Bleach | |
| Water | 800 ml |
| Ethylenediaminetetraacetic acid, disodium salt (dihydrate) | 2 grams |
| Ethylenediaminetetraacetic acid, iron (III) ammonium salt (dihydrate) | 120 grams |
| Potassium bromide | 100 grams |
| Water to make | 1000 ml |
| pH | 5.70 |
| Fixer | |
| Water | 800 ml |
| Sodium thiosulfate | 80.0 grams |
| Sodium sulfite | 5.0 grams |
| Sodium bisulfite | 5.0 grams |
| Water to make | 1000 ml |
| pH | 6.60 |
| Stabilizer | |
| Water | 800 ml |
| Formalin (37 wt %) | 5.0 ml |
| Fuji "Driwell" (a surfactant made by the Fuji Film Co.) | 5.0 ml |
| Water to make | 1000 ml |
| pH | 7.0 |

TABLE 2

| Sample No. | Coupler | Extent of Side Absorption | Cut-off on Short Wavelength Side | Heat Fastness | Remarks |
|---|---|---|---|---|---|
| 201 | A-1 | 0.233 | 0.193 | 79% | Comparison |
| 202 | Illustrative coupler (1) | 0.102 | 0.150 | 90% | Invention |
| 203 | Illustrative coupler (2) | 0.101 | 0.147 | 88% | Invention |
| 204 | Illustrative coupler (24) | 0.093 | 0.120 | 95% | Invention |
| 205 | Illustrative coupler (31) | 0.092 | 0.121 | 90% | Invention |
| 206 | Illustrative coupler (32) | 0.093 | 0.120 | 91% | Invention |

As may be seen from Table 2 that the couplers according to the present invention form dyes which have little side absorption and provide a good cut-off on the short wavelength side.

EXAMPLE 4

Sample No. 214 of Example 2 (multilayer color paper) of European Patent EP 0,355,660A2 (corresponding to JP-A-2-139544 and U.S. Ser. No. 07/393,747) was used for the silver halide color photosensitive material. However, compound III-23 disclosed in the patent as a bisphenol compound, was replaced with compound III-10; the yellow coupler (ExY), the image stabilizer (Cpd-8), the solvent (solv-6) and oxonol dyes indicated below were used. Moreover, the compounds indicated below were used as fungicides (biocide and fungicide), and the cyan coupler in the fifth layer was replaced with equimolar amounts of illustrative couplers (1), (2), (24), (31) and (32).

(ExY) Yellow Coupler
A 1 : 1 (molar) mixture of:

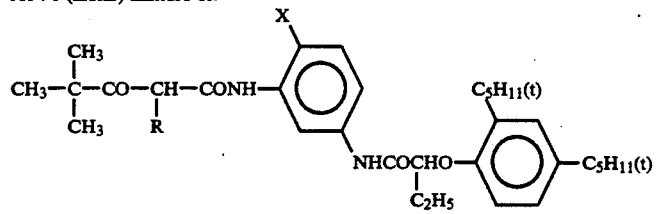

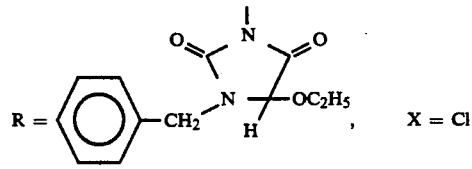

and
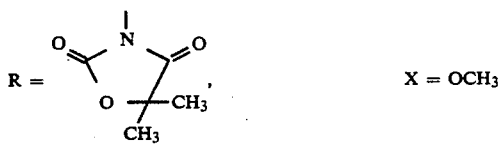    X = OCH$_3$
(Cpd-8) Color Image Stabilizer
A 1 : 1 (molar) mixture of
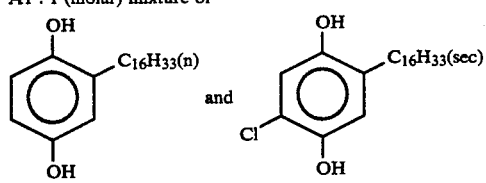
(Cpd-10) Fungicide
    (25.0 mg/m$^2$)
(Cpd-11) Fungicide
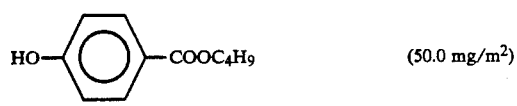    (50.0 mg/m$^2$)
(Solv-6) Solvent
A 9 : 1 (by weight) mixture of:
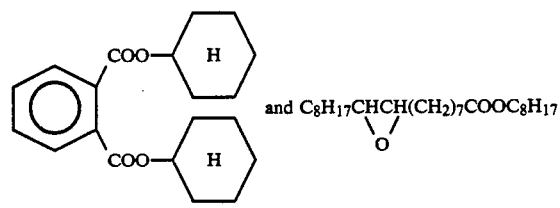
(Oxonol Dyes)
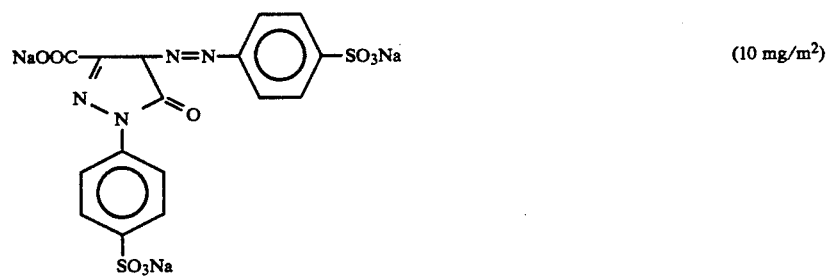    (10 mg/m$^2$)
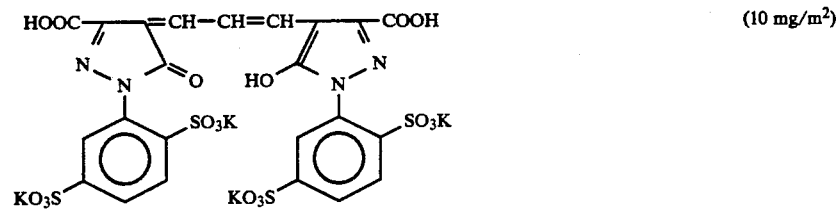    (10 mg/m$^2$)

-continued

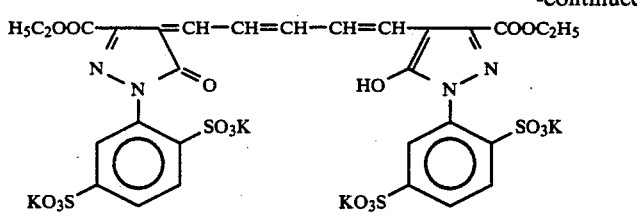 (40 mg/m²)

and

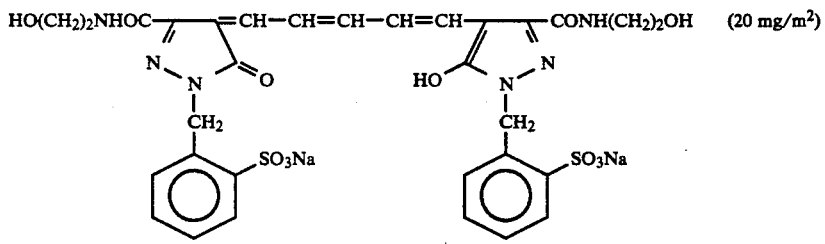 (20 mg/m²)

Furthermore, the color sensitive materials were color developed and processed using the method disclosed in Example 2 of European Patent EP 0,355,660A2.

The results indicated good color (especially green) reproduction.

Accordingly, from the Examples described above it can be seen that it is possible to obtain color images which provide excellent color reproduction according to the present invention.

What is claimed is:

1. A silver halide color photosensitive material comprising a support having thereon at least one layer containing a dye forming coupler represented by formula (I):

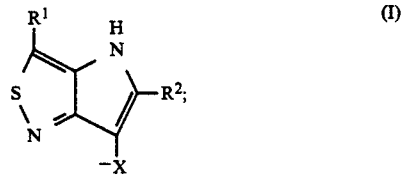

wherein $R^1$ and $R^2$, which may be the same or different, each represents a substituent group, and $R^1$ and $R^2$ substantially cannot be eliminated when the dye forming coupler is reacted with the oxidized species of a primary aromatic amine derivative, and X is a hydrogen atom or a group which can be eliminated by a coupling reaction with the oxidized species of a primary aromatic amine derivative.

2. A silver halide color photosensitive material according to claim 1, wherein $R^1$ and $R^2$ each represents a halogen atom, an aliphatic group, an aromatic group, a heterocyclic group, an alkoxy group, an aryloxy group, an alkenyloxy group, an amino group, an aliphatic or aromatic acyl group, an aliphatic or aromatic oxycarbonyl group, an aliphatic or aromatic acyloxy group, an aliphatic or aromatic oxysulfonyl gorup, an alipahtic or aromatic acylamino group, a carbamoyl group, an aliphatic or aromatic sulfonamido group, a sulfamoyl group, a sulfamido group, an imido group, a ureido group, an aliphatic or aromatic sulfonyl group, an azo group, an aliphatic or aromatic sulfonyloxy group, a phosphoryl group, an aliphatic or aromatic thio group, an alipahtic or aromatic sulfinyl group, a hydroxyl group, a cyano group, a carboxyl group, a nitro group, or a sulfo group.

3. A silver halide color photosensitive material according to claim 1, wherein at least one of $R^1$ and $R^2$ is an electron withdrawing group having a Hammet substitution constant $\sigma_p$ of at least 0.10.

4. A silver halide color photosensitive material according to claim 3, wherein $R_1$ and $R_2$ each is an electron withdrawing group having a Hammet substitution constant $\sigma_p$ of at least 0 10.

5. A silver halide color photosensitive material according to claim 3, wherein said electron withdrawing group having a Hammet substitution constant $\sigma_p$ of at least 0.10 is selected from a cyano group, a carbamoyl group, an alkoxycarbonyl group, an aryloxycarbonyl group, an aliphatic or aromatic acyl group, an aliphatic or aromatic sulfonyl group, a sulfamoyl group, a nitro group, an alkyl group substituted with polyhalogen atoms, a sulfinyl group, a carboxyl group, an azo group, an alkylsulfonyloxy group, a phosphoryl group, a heterocyclic residual group and an aryl group which is substituted with a cyano group, an aliphatic or aromatic sulfonyl group, a nitro group or polyhalogen atoms.

6. A silver halide color photosensitive material according to claim 3, wherein $R_2$ is an electron withdrawing group having a Hammet substitution constant $\sigma_p$ of at least 0.35.

7. A silver halide color photosensitive material according to claim 6, wherein said electron withdrawing group having a Hammet substitution constant $\sigma_p$ of at least 0.35 is selected from a cyano group, a carboxyl group, an azo group, a nitro group, an aliphatic or aromatic acyl group, a carbamoyl group, an alkoxycarbonyl group, an alkylsulfonyloxy group, a phosphoryl group, a heterocyclic residual group, a sulfamoyl group, an aliphatic or aromatic sulfonyl group, an alkyl group substituted with polyhalogen atoms and an aryl group which is substituted with a cyano group, a sulfonyl group, a nitro group or polyhalogen atoms.

8. A silver halide color photosensitive material according to claim 6, wherein $R_2$ is an electron withdrawing group having a Hammet substitution constant $\sigma_p$ of at least 0.60.

9. A silver halide color photosensitive material according to claim 8, wherein said electron withdrawing group having a Hammet substitution constant $\sigma_p$ of at least 0.60 is selected from a cyano group, a nitro group and an aliphatic or aromatic sulfonyl group.

10. A silver halide color photosensitive material according to claim 1, wherein X is a hydrogen atom or a group selected from a halogen atom, an alkoxy group, an aryloxy group, an aliphatic or aromatic acyloxy group, an aliphatic or aromatic sulfonyloxy group, an acylamino group, an aliphatic or aromatic sulfonamido group, an alkoxycarbonyloxy group, an aryloxycarbonyloxy group, an aliphatic or aromatic thio group, a carbamoylamino group, a five-or six-membered nitrogen-containing heterocyclic group, an imido group, an aromatic azo group, and a carboxyl group.

11. A silver halide color photosensitive material according to claim 1, wherein said dye forming coupler is a magenta dye forming coupler or a cyan dye forming coupler.

12. A silver halide color photosensitive material according to claim 1, wherein the amount of said dye forming coupler ranges from $1 \times 10^{-3}$ mol to 1 mol per mol of silver halide.

13. A method for forming color images from a silver halide color photosensitive material comprising a coupling reaction between a dye forming coupler represented by formula (I):

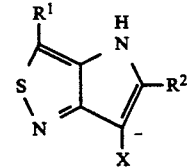

wherein $R^1$ and $R^2$, which may be the same or different, each represents a substituent group, and X is a hydrogen atom or a group which can be eliminated by a coupling reaction with the oxidized species of a primary aromatic amine derivative, and the oxidized species of a primary aromatic amine derivative.

* * * * *